United States Patent
Gutkind et al.

(10) Patent No.: US 9,151,762 B2
(45) Date of Patent: Oct. 6, 2015

(54) IDENTIFICATION OF DSG-3 AS A BIOMARKER FOR THE DETECTION OF METASTASIS IN LYMPH NODES

(75) Inventors: J. Silvio Gutkind, Potomac, MD (US); Vyomesh Patel, Washington, DC (US); Alfredo Molinolo, Rockville, MD (US); Timothy D. Veenstra, Jefferson, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 142 days.

(21) Appl. No.: 13/376,984

(22) PCT Filed: Jun. 11, 2010

(86) PCT No.: PCT/US2010/038325
§ 371 (c)(1),
(2), (4) Date: Dec. 8, 2011

(87) PCT Pub. No.: WO2010/144808
PCT Pub. Date: Dec. 16, 2010

(65) Prior Publication Data
US 2012/0087892 A1    Apr. 12, 2012

Related U.S. Application Data

(60) Provisional application No. 61/186,582, filed on Jun. 12, 2009.

(51) Int. Cl.
| | | |
|---|---|---|
| *G01N 33/574* | (2006.01) | |
| *G01N 33/53* | (2006.01) | |
| *G01N 33/50* | (2006.01) | |
| *C07K 16/28* | (2006.01) | |

(52) U.S. Cl.
CPC ......... *G01N 33/57484* (2013.01); *C07K 16/28* (2013.01); *G01N 33/5005* (2013.01); *G01N 33/5091* (2013.01); *G01N 33/53* (2013.01); *G01N 33/57407* (2013.01); *G01N 2333/705* (2013.01)

(58) Field of Classification Search
None
See application file for complete search history.

(56) References Cited

U.S. PATENT DOCUMENTS

| | | |
|---|---|---|
| 6,969,614 B1 | 11/2005 | Liotta et al. |
| 2006/0019290 A1 | 1/2006 | Godfrey et al. |
| 2006/0068418 A1 | 3/2006 | Godfrey et al. |
| 2006/0223122 A1 | 10/2006 | Fogo et al. |
| 2007/0065859 A1 | 3/2007 | Wang et al. |

FOREIGN PATENT DOCUMENTS

WO    WO 2006/085746    8/2006

OTHER PUBLICATIONS

Chen et al., Oncogene, 2007, vol. 26:467-476.*
Ferris et al., Cancer Res., 2005, vol. 65(6):2147-2156.*
Cui et al., Biosensors and Bioelectronics, 2008, vol. 23:1666-1673.*
Tang et al., Anal. Chem., 2008, vol. 80:8064-8070.*
Mamelle et al., J. Surg., 1994, vol. 168(5):494-498 (abstract).*
Ferris et al., "Molecular Staging of Cervical Lymph Nodes in Squamous Cell Carcinoma of the Head and Neck," *Cancer Research*, vol. 65, pp. 2147-2156, 2005.
Harada et al., "Abnormal desmoglein expression by squamous cell carcinoma cells," *Acta. Derm. Venereol.*, vol. 76, No. 6, pp. 417-420, 1996, Abstract Only.
Nieuwenhuis et al., "Quantitative Molecular Detection of Minimal Residual Head and Neck Cancer in Lymph Node Aspirates," *Clinical Cancer Res.*, vol. 9, pp. 755-761, 2003.
Onishi et al., "Basic and Clinical Studies on Quantitative Analysis of Lymph Node Micrometastasis in Oral Cancer," *Oncol. Rep.*, vol. 11, pp. 33-39, 2004, Abstract Only.
Patel et al., "Proteomic Analysis of Laser-Captured Paraffin-Embedded Tissues: A Molecular Portrait of Head and Neck Cancer Progression," *Clin. Cancer Res.*, vol. 14, pp. 1002-1014, 2008.
Wang et al., "Altered expression of desmocollin 3, desmoglein 3, and β-catenin in oral squamous cell carcinoma: correlation with lymph node metastasis and cell proliferation," *Virchows Arch.*, vol. 451, pp. 959-966, 2007.
Xi et al., "A Combination of Molecular Markers Accurately Detects Lymph Node Metastasis in Non-Small Cell Lung Cancer Patients," *Clinical Cancer Research*, vol. 12, No. 8, pp. 2484-2491, 2006.
Yu et al., "Carbon Nanotube Amplification Strategies for Highly Sensitive Immunodetection of Cancer Biomarkers," *J. Am. Chem. Soc.*, vol. 128, pp. 11199-11205, 2008.

* cited by examiner

*Primary Examiner* — Xiaozhen Xie
(74) *Attorney, Agent, or Firm* — Klarquist Sparkman, LLP

(57) ABSTRACT

Disclosed herein is a method of detecting metastasis of a tumor in a subject, such as metastasis to a lymph node. The method includes directly determining an amount of desmoglein-3 (DSG-3) protein in a sample from the subject (such as a lymph node sample) and comparing the amount of DSG-3 protein to a control, wherein an increase in the amount of DSG-3 protein in the sample relative to the control indicates metastasis of the tumor to the lymph node. The disclosed methods further include selecting a therapy (for example, surgery, lymph node dissection, radiation therapy, chemotherapy, or a combination of two or more thereof) for the subject based on the amount of DSG-3 protein in the sample from the subject.

11 Claims, 10 Drawing Sheets

Primary head and neck cancer lesions

Head and neck cancer lymph node metastasis

IDENTIFICATION OF DSG-3 AS A BIOMARKER FOR THE DETECTION OF METASTASIS IN LYMPH NODES

CROSS REFERENCE TO RELATED APPLICATIONS

This is the §371 U.S. National Stage of International Application No. PCT/US2010/038325, filed Jun. 11, 2010, which was published in English under PCT Article 21(2), which in turn claims the benefit of U.S. Provisional Application No. 61/186,582, filed Jun. 12, 2009, which is incorporated herein in its entirety.

FIELD

This disclosure relates to the field of cancer diagnostics, and in particular to methods for detecting metastasis of a tumor (such as squamous cell carcinoma), for example, to the lymph nodes.

BACKGROUND

Head and neck squamous cell carcinoma (HNSCC) is the sixth most frequent cancer in the United States and the fourth most prevalent cancer among men worldwide. The prognosis of HNSCC patients is relatively poor, due to the advanced nature of the disease at the time of diagnosis. HNSCC frequently metastasizes to the regional lymph nodes, and metastasis is the strongest predictor of disease prognosis and outcome. Current pre-operative clinical methods often misdiagnose the presence or absence of nodal metastasis and the current management of HNSCC commonly includes dissection of neck lymph nodes with pathologic examination.

Metastasis to lymph nodes in HNSCC (and other cancers) is frequently the strongest predictor of disease prognosis and outcome. Lymph nodes that contain tumor cells are designated "positive" lymph nodes. In advanced cases, positive lymph nodes become enlarged and can be detected by palpation. However, small positive nodes, such as nodes that contain tumor cells, but are not yet enlarged, are difficult to identify. Such nodes are referred to as containing "occult" disease. The difficulty of identifying whether a node is negative or contains occult disease complicates treatment decisions. In some cases, lymph nodes that turn out to be negative may be removed unnecessarily, while in other cases, lymph nodes that contain tumor cells are not removed. Other treatment decisions, such as whether to perform additional lymph node dissection and selection of adjuvant treatment are also based on nodal status.

SUMMARY

Due to the difficulty of detecting occult metastasis to lymph nodes, there is a need to identify molecular markers that accurately detect lymph node metastasis of HNSCC and other cancers. Disclosed herein is a method of detecting metastasis of a tumor in a subject, such as metastasis to a lymph node. The method includes directly determining an amount of desmoglein-3 (DSG-3) protein in a sample from the subject (such as a lymph node sample) and comparing the amount of DSG-3 protein to a control, wherein an increase in the amount of DSG-3 protein in the sample relative to the control (for example, an increase of about 1.5-fold to 10-fold) indicates metastasis of the tumor. In some examples, the method further includes providing results of the test to a user (such as a clinician or other health care worker) in the form of an output.

The disclosed methods directly measure the amount of DSG-3 protein present in the sample (for example, using an immunoassay), instead of relying on an indirect assay (such as quantification of mRNA). Direct detection of DSG-3 protein is surprisingly more sensitive than indirect detection of DSG-3 RNA. In some examples, the disclosed methods provide about 100-fold greater sensitivity in detecting DSG-3 protein than methods which detect DSG-3 RNA (such as quantitative PCR methods).

In some examples, the sample (such as a biopsy, aspirate, or isolated cells) is from a lymph node to which metastatic spread of the tumor would be expected (such as regional lymph nodes). For example, if the tumor is HNSCC, then the sample may include one or more cervical lymph nodes, while if the tumor is lung SCC, the sample may include one or more hilar or mediastinal lymph nodes. In a particular example, the sample includes a sentinel lymph node.

In particular examples, the amount of DSG-3 protein is determined by immunoassay (such as Western blotting, immunohistochemistry, ELISA, or electrochemical immunoassays). In a particular example, the amount of DSG-3 protein is determined by ELISA, for example, using an antibody that specifically binds an epitope in the DSG-3 extracellular domain (such as BAF1720, R&D Systems, Minneapolis, Minn.). In other examples, the amount of DSG-3 protein is determined by electrochemical immunoassay, for example using an electrode including gold-nanoparticies conjugated to an anti-DSG-3 antibody. In particular examples, the method is highly sensitive, for example, detecting DSG-3 protein in about 5000 lymph node cells or less (such as less than 5000, 1000, 200, 100, 50, 10, or less lymph node cells in a sample).

The disclosed methods further include selecting a therapy (for example, surgery, lymph node dissection, radiation therapy, chemotherapy, or a combination of two or more thereof) for the subject based on the amount of DSG-3 protein in the sample from the subject. In particular examples, if the amount of DSG-3 protein is increased relative to the control, the selected therapy includes lymph node dissection (for example, radical neck dissection, modified radical neck dissection, or selective neck dissection if the tumor is HNSCC). In additional examples, the disclosed methods include providing the selected therapy to the subject.

The foregoing and other features of the disclosure will become more apparent from the following detailed description, which proceeds with reference to the accompanying figures.

BRIEF DESCRIPTION OF THE DRAWINGS

FIG. 4 is a series of digital images showing DSG-3 protein detected by IHC in different tumor types.

DETAILED DESCRIPTION

I. Abbreviations

Figure 1A:
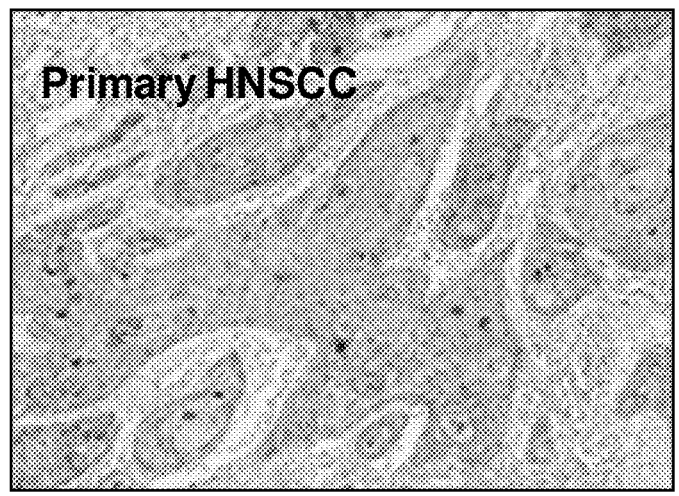
FIG. 1A is a series of digital images of DSG-3 protein detected by immunohistochemistry (HIC) in primary HNSCC and normal (−LN) and invaded (+LN) lymph node sections.
Figure 1A:
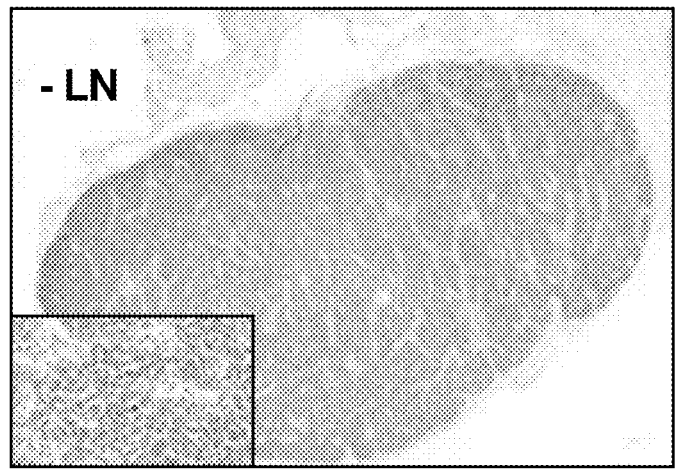
Figure 1A:

AuNP: gold nanoparticle
DSG-3: desmoglein-3
ELISA: enzyme-linked immunosorbant assay
HNSCC: head and neck squamous cell carcinoma
IHC: immunohistochemistry
LN: lymph node
OSCC: oral squamous carcinoma
SCC: squamous cell carcinoma
TCL: total cell lysate

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antibody: A polypeptide including at least a light chain or heavy chain immunoglobulin variable region which specifically recognizes and binds an epitope of an antigen, such as DSG-3 or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Antibodies of the present disclosure include those that are specific for DSG-3.

The term antibody includes intact immunoglobulins, as well the variants and portions thereof, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds DSG-3 will have a specific $V_H$ region and the $V_L$ region sequence, and thus specific CDR sequences. Antibodies with different specificities (such as different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen, which are then purified from the mammal's serum.

A "chimeric antibody" has framework residues from one species, such as human, and CDRs (which generally confer antigen binding) from another species, such as a murine antibody that specifically binds a DSG-3 molecule.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one example, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Control: A "control" refers to a sample or standard used for comparison with an experimental sample. In some embodiments, the control is a sample obtained from a healthy subject or a non-tumor or non-metastatic tissue sample obtained from a patient diagnosed with cancer (such as a normal (non-metastatic) lymph node). In some embodiments, the control is a historical control or standard reference value or range of values (such as a previously tested control sample, such as a group of cancer patients with metastatic disease, or group of samples that represent baseline or normal values, such as the amount of DSG-3 protein in non-metastatic lymph nodes).

Desmoglein-3 (DSG-3): A member of the desmoglein subfamily of the cadherin cell adhesion molecule superfamily. DSG-3 is a calcium-binding transmembrane glycoprotein component of desmosomes in vertebrate epithelial cells. This protein is the autoantigen of the autoimmune disease pemphigus vulgaris, and is also known as pemphigus vulgaris antigen, or PVA.

Nucleic acid and protein sequences for DSG-3 are publicly available. For example, GENBANK® Accession Nos.: NM_001944, M76482, AK290367, and BX538327 disclose exemplary nucleic acid sequences that encode human DSG-3, and GENBANK® Accession Nos.: NP_001935, AAA60230, BAF83056, and CAD98098 disclose exemplary human DSG-3 amino acid sequences, all of which are incorporated by reference as included in GENBANK® on Jun. 12, 2009.

In one example, DSG-3 includes a full-length wild-type (or native) sequence, as well as DSG-3 allelic variants that retain the ability to be expressed at increased levels in a metastasis, such as a squamous cell carcinoma lymph node metastasis. In certain examples, DSG-3 has at least 80% sequence identity, for example at least 85%, 90%, 95%, or 98% sequence identity to a publicly available DSG-3 sequence.

Directly determine amount of a protein: Measuring an amount of a protein itself (for example, using an immunoassay, such as ELISA) instead of measuring an indirect marker related to the protein (such as mRNA). In a particular example, directly determining an amount of a protein includes determining the amount of DSG-3 protein in a sample by conventional ELISA or electrochemical immunoassay (for example, utilizing a gold-nanoparticle electrode or a carbon nanotube electrode).

Head and neck squamous cell carcinoma (HNSCC): The term head and neck cancer refers to a group of biologically similar cancers originating from the upper aerodigestive tract, including the lip, oral cavity, nasal cavity, paranasal sinuses, pharynx, and larynx. Most head and neck cancers are squamous cell carcinomas, originating from the mucosal lining (epithelium) of these regions. Head and neck squamous cell carcinomas often spread to the lymph nodes of the neck, and this is often the first (and sometimes only) manifestation of the disease at the time of diagnosis. HNSCC is strongly associated with certain environmental and lifestyle risk factors, including tobacco smoking, alcohol consumption, and certain strains of the human papillomavirus. HNSCC can be curable if detected early, usually with some form of surgery, although chemotherapy and radiation therapy may also be needed.

Immunoassay: A method of detecting the presence or amount of a protein (as opposed to an mRNA encoding a protein) in a sample. An immunoassay detects a protein (for example, an antigen, such as DSG-3) in a sample by detecting interaction of the antigen with a specific binding agent, such as an antibody. A sample including an antigen (such as DSG-3) is incubated with an antibody under conditions permitting antibody-antigen binding. Antibody-antigen binding can be detected by means of a detectable label conjugated to the antibody (such as a primary antibody), by means of a detectable label conjugated to a secondary antibody, which is raised against the primary antibody, or by means of a detectable label conjugated directly or indirectly to a second antibody that binds the antigen. Exemplary detectable labels that can be used for immunoassays include, but are not limited to, radioactive isotopes, fluorochromes (such as fluorescein, fluorescein isothiocyanate, and rhodamine), magnetic labels, and enzymes (such as horseradish peroxidase or alkaline phosphatase). Particular examples of immunoassays include without limitation, ELISA, Western blotting, immunohistochemistry, electrochemical immunoassay, radioimmunoassay, and magnetic immunoassay. In a specific non-limiting example, an immunoassay used to detect DSG-3 protein includes a conventional ELISA utilizing an anti-DSG-3 antibody (for example, anti-human DSG-3, such as catalog number BAF1720, R&D Systems, Minneapolis, Minn.).

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins. In one example, an isolated cell is a lymph node cell that is substantially separated from other cell subtypes.

Lymph node: A mass of lymphatic tissue surrounded by a capsule of connective tissue located in the lymphatic system. Lymph nodes are part of the immune system and function to remove invading organisms (such as bacteria) or abnormal cells (such as cancer cells) from the lymph fluid. The lymph nodes are usually present in clusters, including the cervical lymph nodes, hilar lymph nodes, mediastinal lymph nodes, and axillary lymph nodes.

Lymph nodes are usually the first site of metastasis of a tumor. The initial metastasis will usually be to one or more lymph nodes that are drained by the portion of the lymphatic system where the primary tumor is located. These lymph nodes are referred to as "regional lymph nodes." Thus, the regional lymph nodes vary, depending on the location of the tumor. For example, for head and neck cancer, the cervical lymph nodes are considered regional lymph nodes, while for lung cancer, the hilar and mediastinal lymph nodes are considered regional lymph nodes. The first lymph node along one or more paths of lymphatic drainage away from the primary tumor is referred to as a "sentinel lymph node."

Metastasis: The spread of a tumor (such as one or more tumor cell) from one part of the body to another. Tumors formed from cells that have spread (metastases) are called secondary tumors and contain cells that are like those in the original (primary) tumor. In some examples, a metastasis includes the presence of tumor cells in one or more lymph nodes, such as a lymph node near the site of a primary tumor.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation.

Sample: A biological specimen containing genomic DNA, RNA (including mRNA), protein, or combinations thereof, obtained from a subject. In some examples, a sample includes lymph node tissue, such as cervical lymph node. In one example, a sample includes a lymph node biopsy (such as a fine needle aspirate), a dissected lymph node or portion thereof, or cells isolated from a lymph node.

Specifically binds: A term that refers to the binding of agent that preferentially binds to a defined target (such as an antibody to a specific antigen or a nucleic acid probe to a specific nucleic acid sequence). With respect to an antigen, "specifically binds" refers to the preferential association of an antibody or other ligand, in whole or part, with a specific polypeptide (such as DSG-3 or a portion thereof).

Squamous cell carcinoma (SCC): A form of cancer of the carcinoma type that may occur in many different organs, including the skin, lips, mouth, esophagus, urinary bladder, prostate, lungs, vagina, and cervix. It is a malignant tumor of squamous epithelium (epithelium that shows squamous cell differentiation). A carcinoma can be characterized as either in situ (confined to the original site) or invasive, depending on whether the cancer invades underlying tissues; only invasive cancers are able to spread to other organs and cause metastasis.

Squamous cell carcinoma is the second most common cancer of the skin (after basal cell carcinoma but more common than melanoma). It usually occurs in areas exposed to the sun, and can generally be treated by excision only. Sunlight exposure and immuno-suppression are risk factors for SCC of the skin. The risk of metastasis is larger with SCC than with basal cell carcinoma.

Most cases of head and neck cancer (cancer of the mouth, nasal cavity, throat and associated structures) are due to squamous cell carcinoma. Symptoms may include a poorly healing mouth ulcer, a hoarse voice or other persistent problems in the area. Treatment is usually with surgery (which may be extensive) and radiotherapy. Risk factors include smoking and alcohol consumption.

Esophageal cancer may be due to either SCC or adenocarcinoma (EAC). SCCs tend to occur closer to the mouth, while adenocarcinomas occur closer to the stomach. Dysphagia (difficulty swallowing, solids worse than liquids) and odynophagia are common initial symptoms. If the disease is localized, esophagectomy may offer the possibility of a cure. If the disease has spread, chemotherapy and radiotherapy are commonly used.

SCC also occurs in the lung. When associated with the lung, it often causes ectopic production of parathyroid hormone-related protein, resulting in hypercalcemia.

When associated with the prostate, squamous cell carcinoma is very aggressive in nature. It is difficult to detect, as there is no increase in prostate specific antigen level, meaning that the cancer is often diagnosed at an advanced stage.

Vaginal squamous cell carcinoma spreads slowly and usually stays near the vagina, but may spread to the lungs and liver. This is the most common type of vaginal cancer.

Subject: Living multi-cellular vertebrate organisms, a category that includes human and non-human mammals (such as laboratory or veterinary subjects).

III. Methods for Detecting Metastasis of a Tumor

HNSCC (and other malignant tumors) frequently metastasize to the regional lymph nodes, and lymph node involvement is frequently the strongest predictor of disease prognosis and outcome. However, due to the low sensitivity of detecting lymph node metastases using current clinical methods, the presence of nodal metastasis is often missed in many patients. The inventors have identified DSG-3 protein as highly expressed in tumors of squamous epithelial cell origin and in some adenocarcinomas (for example, breast, gastric, colon, and thyroid adenocarcinoma). DSG-3 protein is also expressed in invaded lymph nodes, but not normal lymph nodes, and is an indicator of metastatic spread of the primary tumor. Thus, detection of DSG-3 protein in lymph nodes from a subject with a tumor indicates metastasis of the tumor in the subject.

The disclosed methods utilize direct detection of DSG-3 protein in a sample (such as a lymph node sample, for example from a subject having a tumor). Directly detecting protein (rather than a nucleic acid, such as mRNA) is advantageous because there is frequently discordance or lack of correlation between transcript levels and protein abundance, particularly in cancer (see, e.g., Nagaraja et al., *Oncogene* 25:2328-2338, 2006; Chen et al., *J. Proteome Res.* 5:2727-2742, 2006). Thus, the amount of a protein present in a sample may provide a more accurate reflection of biological processes, such as those that contribute to tumor development or metastasis.

In addition, immunoassays for the direct detection of protein amounts are highly sensitive, often achieving detection of as little as 10-100 pg/ml by ELISA and as little as 0.5 pg/ml by electrochemical immunoassay (for example for detection of serum proteins). See, e.g., Liew et al., *BioTechniques* 42:327-333, 2007; Azam et al., *Toxicol.* 206:285-298, 2005; Yu, et al., *J. Am. Chem. Soc.* 128:11199-11205, 2006; Mani et al., *ACS Nano* 3:585-594, 2009; Malhotra et al., *Anal. Chem.* 82:3118-3123, 2010; all of which are incorporated by reference herein. Immunoassays for direct detection of protein can also detect as few as 1-10 cells in a sample expressing a particular protein (such as DSG-3 protein). Thus, direct detection of a protein can provide information regarding even small changes in protein amount (for example, a small increase in total amount of a particular protein in a sample or an increased amount of a protein in a limited number of cells in a sample), which may have biological significance. In addition, direct detection of a protein does not require any amplification steps (as are required for detecting RNA), avoiding the potential introduction of amplification bias. Finally, practical considerations, such as those of much greater stability of protein than RNA in a sample, make direct detection of protein advantageous, for example, in handling (such as absence of the need for handling samples in an RNAse-free environment) and shorter processing time of samples in the clinical and laboratory setting.

Disclosed herein are methods for detecting metastasis of a tumor (for example, metastasis to a lymph node), including detecting an increase (such as a statistically significant increase) in the amount of DSG-3 protein in a lymph node sample. In one example, metastasis of a tumor (such as a SCC, for example HNSCC or lung SCC) is detected by directly determining whether a sample from the subject (such as a lymph node sample) has an increased amount (such as an increase of at least about 1.5-fold, 2-fold, 3-fold, 4-fold, 5-fold, 10-fold, or more) of DSG-3 protein relative to a control (such as a non-metastatic sample of the same tissue type or a reference value or range of values for DSG-3 protein amount in an appropriate normal tissue), for example using an antibody that specifically binds DSG-3. Thus, for example, if the sample from the subject is a lymph node sample, the control can be a normal (non-metastatic) lymph node, for example from the same subject or a subject without cancer, or a reference value representing DSG-3 protein amount expected in a normal lymph node sample. In some embodiments, the control is a lymph node sample obtained from a healthy subject or a non-metastatic lymph node sample obtained from a patient diagnosed with cancer. In other embodiments, the control is a historical control or standard reference value or range of values (such as a previously tested control sample, such as a group of samples that represent baseline or normal values, such as the DSG-3 protein amount in non-metastatic lymph node tissue).

In particular examples, the methods disclosed herein provide for highly sensitive detection of DSG-3 protein in a biological sample. The assay in some examples is an immunoassay, for example, an assay that exclusively relies on immunological interaction of an antibody with the DSG-3 protein (for example, without detection of an mRNA, such as without nucleic acid amplification). For example, utilizing a conventional ELISA assay (without nucleic acid amplification), as little as 0.3 ng of purified DSG-3 protein (such as about 0.3 ng to about 300 ng of DSG-3) can be detected in a sample. In other examples, a small number of tumor cells expressing DSG-3 protein (such as about 3 cells to 300 cells) can be detected in a mixture with a large number of cells which do not express detectable amounts of DSG-3 protein (such as about 1000 to about 10,000 normal cells). In a particular example, an ELISA assay can detect as little as three DSG-3 protein expressing cells in 10,000 non-DSG-3 protein expressing cells, for example in a crude protein preparation (such as a total cell lysate). In further examples, using electrochemical immunoassays (such as carbon nanotube or gold nanoparticle immunosensors), as little as about 5 fg to 40 fg of a protein can be detected in a sample. Thus, this method is at least as sensitive as ELISA, and can detect as few as 1-3 cells expressing a particular protein (such as DSG-3), even when the cells are present in a complex mixture, such as a population of cells that do not express DSG-3 protein (e.g., 10 or more cells, such as 100, 1000, 10,000, 100,000, 1,000,000, or more cells that do not express DSG-3).

In some examples, metastasis of a tumor to a lymph node is indicated by detecting an increase in DSG-3 protein in about 5000 cells or less (such as about 5000, 1000, 300, 200, 100, 50, 30, 10, 9, 8, 7, 6, 5, 4, 3, 2, or 1 cell) in a lymph node sample. In other examples, metastasis of a tumor to a lymph node is indicated by detecting an increase in DSG-3 protein in about 1-5000 cells, such as about 1-1000 cells, about 1-500 cells, about 1-300 cells, about 1-100 cells, about 1-50 cells, about 3-300 cells, about 1-10 cells, about 3-10 cells, or even about 1-3 cells.

Methods of directly determining the amount of a protein (such as DSG-3) in a sample are well known to those of skill in the art. In some examples, the methods include immunoassays, such as ELISA, immunohistochemistry, electrochemical immunoassay, Western blotting, or radioimmunoassay. Exemplary methods are discussed in more detail below.

A. Biological Samples

The disclosed methods include determining an amount of DSG-3 in a biological sample from a subject. In particular examples, the biological sample is a lymph node sample (such as a lymph node, lymph node biopsy, or lymph node cells) from a lymph node to which metastatic spread of the tumor would be expected (such as regional lymph nodes). One of skill in the art can select lymph nodes based on the type and location of the primary tumor in the subject. One or more samples (such as samples from multiple lymph nodes) may be collected from a subject.

In some examples, the sample may be from a sentinel lymph node (SLN). The SLN is the first lymph node along one or more paths of lymphatic drainage away from the primary tumor before lymphatic flow drains secondarily into the remaining regional LNs. The commonly used methods for identifying and locating the SLN employ peritumoral injections of either isosulfan blue dye, or a radionuclide-labeled sulfur or albumin colloid (radiocolloid). The dye or radiocolloid serves as a tracer of lymphatic flow away from a tumor. In the blue dye technique, the SLN is detected by direct visualization, which requires blind dissection of tissue until the "dyed" SLN is detected. In the radiocolloid technique, the SLN is located based on a localized accumulation of radioactivity that is detected using a hand-held gamma ray counter (see, for example, Alazraki et al., *Radiol. Clin. North Am.* 39:947-956, 2001).

In other examples, if the primary tumor is a HNSCC tumor, the lymph node sample may be obtained from one or more regional lymph nodes, such as a cervical lymph node (for example, preauricular, submental, submandibular, upper jugular chain, upper spinal accessory, jugulodigastric, occipital, mid-spinal accessory, lower spinal accessory, midjugular chain, jugulo-omohyoid, or lower jugular chain lymph nodes). The particular cervical lymph nodes may be chosen based on the primary site of the HNSCC tumor, for example, as shown in Table 1. The lymph node sample may be obtained from more distant lymph nodes, if distant metastasis of the tumor is suspected. In HNSCC, more distant lymph nodes that may be sampled include the supraclavicular lymph nodes.

TABLE 1

Exemplary lymphatic spread from common HNSCC sites

| Primary Tumor Site | Lymph Node Group |
|---|---|
| Lower lip, anterior oral cavity, skin | Submental |
| Lower lip, oral cavity, facial skin | Submandibular |
| Oral cavity, oropharynx, hypopharynx | Subdigastric |
| Hypopharynx, base of tongue, larynx, thyroid | Midcervical |
| Hypopharynx, thyroid | Lower cervical |
| Nasopharynx, hypopharynx, thyroid | Posterior triangle |

In other examples, if the primary tumor is a lung SCC tumor, the lymph node sample may be obtained from one or more regional lymph nodes, such as hilar, mediastinal, or supraclavicular lymph nodes (for example, hilar, interlobar, lobar, segmental, subsegmental, inferior mediastinal, or superior mediastinal lymph nodes.). The lymph node sample may be obtained from more distant lymph nodes, if distant metastasis of the tumor is suspected. In lung SCC, more distant lymph nodes that may be sampled include the scalene, supraclavicular, or cervical lymph nodes.

In some examples, cells (for example cells from a lymph node section) may be collected by laser capture microdissection (LCM). Methods of LCM are well known in the art (see, e.g., U.S. Pat. Nos. 5,843,657 and 6,969,614). Briefly a laser beam is used to focally activate a transfer film that specifically bonds to cells in a tissue section (for example, a lymph node section) identified and targeted by microscopy. The transfer film attached to the cells is then lifted off the tissue section, leaving non-targeted cells behind. The cells collected by LCM can then be analyzed for DSG-3 protein, for example by immunoassay methods described herein.

The disclosed methods include comparing the amount of DSG-3 protein in a sample to a control, wherein an increase in the amount of DSG-3 in the sample relative to the control indicates metastasis of the tumor. The control can be any suitable control against which to compare amount of DSG-3 protein in a sample from a subject. In some embodiments, the control is non-metastatic lymph node (such as normal lymph node tissue or cells). In some examples, the non-metastatic lymph node is obtained from the same subject, such as a non-metastatic lymph node that is near or adjacent to the lymph node from which the sample is obtained. In other examples, the non-metastatic lymph node is obtained from a healthy control subject without cancer. In some embodiments, the control is a reference value or ranges of values. For example, the reference value can be derived from the average lymph node DSG-3 protein values obtained from a group of healthy control subjects or non-metastatic lymph nodes from a group of cancer patients.

The disclosed methods can be used to diagnose metastasis of a carcinoma or other solid tumor. Examples of such solid tumors include head and neck squamous cell carcinoma, lung squamous cell carcinoma, rectal, prostate, colon, and breast carcinoma, synovioma, mesothelioma, ovarian cancer, hepatocellular carcinoma, squamous cell carcinoma, basal cell carcinoma, adenocarcinoma, sweat gland carcinoma, sebaceous gland carcinoma, papillary carcinoma, papillary adenocarcinoma, medullary carcinoma, bronchogenic carcinoma, gastric carcinoma, thyroid carcinoma, renal cell carcinoma, hepatoma, bile duct carcinoma, choriocarcinoma, Wilms' tumor, cervical cancer, testicular tumor, bladder carcinoma, and ependymoma. In particular examples, the tumor is a tumor that expresses DSG-3 protein.

In a particular example, the tumor includes a squamous cell carcinoma (such as head and neck squamous cell carcinoma or lung squamous carcinoma). In some examples, the tumor is a HNSCC, for example, oral squamous carcinoma (such as tumors of the lip, tongue, hard palate, floor of mouth, or buccal mucosa), oropharyngeal squamous carcinoma (such as tumors of the soft palate, base of the tongue, or tonsillar region), hypopharyngeal squamous carcinoma (such as tumors of the pyriform sinus, posterior pharyngeal wall, or postcricoid region), nasopharyngeal squamous carcinoma (such as tumors of the maxillary antrum), or laryngeal squamous carcinoma. In other examples, the tumor is a lung SCC.

In further examples, the tumor includes colon adenocarcinoma, gastric adenocarcinoma, breast carcinoma, or thyroid adenocarcinoma.

IV. Detection of DSG-3 Protein

DSG-3 protein level (as opposed to nucleic acid, such as mRNA levels) is directly analyzed and quantitated in the disclosed methods. Suitable biological samples include samples containing protein obtained from a lymph node (such as a lymph node biopsy or isolated lymph node cells) of a subject having a tumor, from non-metastatic lymph node of the subject, and/or protein obtained from one or more lymph node samples of cancer-free subjects. An increase in the amount of DSG-3 protein in a lymph node sample from the subject relative to a control (such as an increase of at least about 1.5-fold, 2-fold, 3-fold, 4-fold, 5-fold, 10-fold, or more), indicates metastasis of the tumor, as described above.

DSG-3 protein can be detected and quantitated in a sample (such as a lymph node sample) using routine immunoassay methods such as Western blot, ELISA, immunohistochemistry, mass spectrometry, or electrochemical immunoassays. Detection and quantitation of the protein refers to measuring the DSG-3 protein itself, as opposed to measuring an indirect marker of protein expression (such as mRNA). Antibodies specific for DSG-3 can be used for detection and quantitation of DSG-3 by immunoassay methods that are well known in the art, such as those presented in Harlow and Lane (*Antibodies, A Laboratory Manual*, CSHL, New York, 1988). Methods of constructing such antibodies are known in the art. In addition, such antibodies may be commercially available. Exemplary commercially available antibodies include DSG-3 antibodies, such as catalog numbers BAF1720 and MAB1720 (R&D Systems, Minneapolis, Minn.); catalog number 32-6300 (Invitrogen/Life Technologies, Carlsbad, Calif.); catalog numbers sc-20116, sc-14866, and sc-14867 (Santa Cruz Biotechnology, Santa Cruz, Calif.); and catalog numbers ab62440 and ab14416 (Abcam, Cambridge, Mass.).

In some examples, DSG-3 protein is present in the sample (such as a lymph node sample) as part of a mixture of proteins, such as in an intact cell (for example in a tissue section, such as for immunohistochemistry) or a crude protein mixture (such as a cell lysate). In one example, a total cell lysate is prepared, which includes a mixture of proteins present in the sample (such as DSG-3 and other proteins). In other examples, DSG-3 protein is purified before detection. Methods of purifying proteins are well known in the art, and include antibody-based methods, such as immunoprecipitation or use of an antibody affinity column.

Any standard immunoassay format (such as ELISA, Western blot, or radioimmunoassay) can be used to measure DSG-3 protein levels. Thus, in one example, polypeptide levels of DSG-3 in a sample including lymph node tissue or cells can readily be evaluated using these methods. Immunohistochemical techniques can also be utilized for DSG-3 protein quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

In one example, DSG-3 protein can be detected by incubating the biological sample with an antibody (such as a primary antibody) that specifically binds to DSG-3. The primary antibody can include a detectable label. For example, the primary antibody can be directly labeled, or the sample can be subsequently incubated with a secondary antibody that is labeled (for example with a fluorescent or enzymatic label). The label can then be detected, for example by microscopy, ELISA, flow cytometry, or spectrophotometry. In another example, the biological sample is analyzed by Western blotting for detecting DSG-3 protein.

In one example, the DSG-3 antibody is directly labeled with a detectable label. In another example, the DSG-3 antibody (the primary antibody) is unlabeled and a second antibody or other molecule that can bind the DSG-3 antibody is labeled. As is well known to one of skill in the art, a second antibody is chosen that is able to specifically bind the specific species and class of the first antibody. For example, if the first antibody is a human IgG, then the secondary antibody can be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary magnetic agent is gadolinium; and non-limiting exemplary radioactive labels include $^{125}$I, $^{131}$I, $^{35}$S or $^{3}$H.

In a particular example, an ELISA method effective for the detection of DSG-3 can, for example, be as follows: 1) bind the sample (such as a total cell lysate or isolated DSG-3 protein from a lymph node sample) to a substrate; 2) contact the bound sample with an anti-DSG-3 antibody; 3) contact the above with a secondary antibody which is reactive with the anti-DSG-3 antibody, where the secondary antibody is bound to a detectable moiety (for example, horseradish peroxidase or alkaline phosphatase conjugated secondary antibody); 4) contact the above with the substrate for the enzyme; and 5) measure signal development (for example color or luminescence). In a particular example, the ELISA method utilizes an antibody that specifically binds one or more epitope in the DSG-3 extracellular domain, such as antibody BAF1720 (R&D Systems, Minneapolis, Minn.).

In another example, a sandwich ELISA can be used to detect the presence or amount of an antigen in a sample, such as a DSG-3. In this method, a solid surface is first coated with a DSG-3 antibody. The test sample, containing the antigen (such as a total cell lysate or isolated DSG-3 protein from a lymph node sample) is then added and the antigen is allowed to react with the bound antibody. Any unbound antigen is washed away. A known amount of enzyme-labeled DSG-3 antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the DSG-3 present in the sample tested.

In an alternative example, DSG-3 protein can be assayed in a biological sample by a competition immunoassay utilizing DSG-3 protein standards labeled with a detectable substance and an unlabeled antibody that specifically binds DSG-3. In this assay, the biological sample (such as a total cell lysate or isolated DSG-3 protein from a lymph node sample), the labeled DSG-3 protein standards and the antibody that specifically binds DSG-3 are combined and the amount of labeled DSG-3 standard bound to the unlabeled antibody is determined. The amount of DSG-3 protein in the biological sample is inversely proportional to the amount of labeled DSG-3 protein standard bound to the antibody that specifically binds DSG-3.

Quantitative spectroscopic methods, such as MALDI or SELDI, can also be used to analyze DSG-3 protein amount in a sample (such as a lymph node sample). In one example, surface-enhanced laser desorption-ionization time-of-flight (SELDI-TOF) mass spectrometry is used to detect protein, for example by using the ProteinChip™ (Ciphergen Biosystems, Palo Alto, Calif.). Such methods are well known in the art (for example see U.S. Pat. Nos. 5,719,060, 6,897,072, and 6,881,586). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as DSG-3 protein. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as DSG-3 protein) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector.

In an additional example, the method may include detection of DSG-3 protein in a sample using an electrochemical immunoassay method. See, e.g., Yu et al., *J. Am. Chem. Soc.* 128:11199-11205, 2006; Mani et al., *ACS Nano* 3:585-594, 2009; Malhotra et al., *Anal. Chem.* 82:3118-3123, 2010. In this method, an antibody (such as an anti-DSG-3 antibody) is conjugated to terminally carboxylated single-wall carbon nanotubes (SWNT), multi-wall carbon nanotubes (MWCNT), or gold nanoparticles (AuNP), which are attached to a conductive surface. A sample (such as a lymph node sample, for example a total cell lysate) is contacted with the SWNTs, MWCNTs, or AuNPs, and protein in the sample (such as DSG-3) binds to the primary antibody (such as an anti-DSG-3 antibody). A second antibody conjugated directly or indirectly to a redox enzyme (such as horseradish peroxidase (HRP), cytochrome c, myoglobin, or glucose oxidase) binds to the primary antibody or to DSG-3 protein (for example, in a "sandwich" assay). In some examples, the second antibody is conjugated to the enzyme. In other examples, the second antibody and the enzyme are both conjugated to a support (such as a magnetic bead). Signals are generated by adding enzyme substrate (e.g. hydrogen peroxide if the enzyme is HRP) to the solution bathing the sensor and measuring the current produced by the catalytic reduction.

In a particular example, the method includes a first DSG-3 antibody attached to a AuNP sensor surface. A sample (such as a lymph node sample) is contacted with the AuNP sensor including the first antibody. After DSG-3 binds to the first (capture) antibody ($Ab_1$) on the electrode, a horseradish peroxidase (HRP)-labeled second DSG-3 antibody (HRP-$Ab_2$) or beads conjugated to both a second DSG-3 antibody and HRP are incubated with the sensor, allowing the second antibody to bind to DSG-3. Biocatalytic electrochemical reduction produces a signal via reduction of peroxide activated enzyme following addition of hydrogen peroxide. Use of HRP is advantageous for arrays since immobilization of the electroactive enzyme label on the electrode eliminates electrochemical crosstalk between array elements, which can occur when detecting soluble electroactive product.

V. Selection of Therapy

In some examples, the methods disclosed herein include selecting a therapy for a subject with cancer. The method includes determining an amount of DSG-3 protein in a sample (such as one or more lymph nodes or portions thereof) from a subject, comparing the amount of DSG-3 protein in the sample to a control (such as a lymph node from an individual without cancer, a non-metastatic lymph node from an individual with cancer, or a reference value), wherein an increase in the amount of DSG-3 protein in the sample indicates metastasis of the tumor, and based on the amount of DSG-3 protein in the sample, selecting a therapy for the subject. Examples of therapies include, but are not limited to, surgical treatment for removal or reduction of the tumor (such as surgical resection, cryotherapy, or chemoembolization), lymph node dissection, radiation therapy, and anti-tumor pharmaceutical treatments which can include radiotherapeutic agents, anti-neoplastic chemotherapeutic agents, antibiotics, alkylating agents and antioxidants, kinase inhibitors, and other agents.

After a histologic diagnosis has been established and tumor extent determined, the selection of appropriate treatment for a specific cancer depends on a complex array of variables, including tumor site, relative morbidity of various treatment options, patient performance and nutritional status, concomitant health problems, social and logistic factors, previous primary tumors, and patient preference. Treatment planning generally requires a multidisciplinary approach involving specialist surgeons and medical and radiation oncologists.

Factors that affect choice and type of treatment include the site and stage of the primary tumor. For example, the TNM system is used to assess prognosis and develop a treatment plan. T refers to the tumor site, N refers to the status of the regional lymph nodes (such as the cervical lymph nodes in the case of HNSCC), and M refers to presence or absence of distant metastases. Exemplary TNM stages for head and neck tumors include:

T—Primary Tumor
$T_{is}$: carcinoma in situ
$T_0$: no evidence of primary tumor
$T_1$: tumor 2 cm or less in greatest dimension
$T_2$: tumor larger than 2 cm, but not larger than 4 cm
$T_3$: tumor larger than 4 cm
$T_4$: tumor with extension to bone, muscle, skin, neck
N—Regional Lymph Node Involvement
$N_0$: no evidence of regional lymph node involvement
$N_1$: evidence of involvement of movable homolateral regional lymph node smaller than 3 cm
$N_{2a}$: evidence of involvement of movable homolateral regional lymph node 3-6 cm
$N_{2b}$: evidence of involvement of multiple homolateral regional lymph nodes smaller than 6 cm
$N_{2c}$: evidence of involvement of contralateral or bilateral regional lymph nodes smaller than 6 cm
$N_3$: any lymph node larger than 6 cm
M—Distant Metastases
$M_0$: no evidence of distant metastases
$M_1$: evidence of distant metastases Staging of a HNSCC tumor can be defined by the TNM status. Stage I includes $T_1/N_0/M_0$ tumors, Stage II includes $T_2/N_0/M_0$ tumors, Stage III includes $T_3/N_0/M_0$ and $T_3/N_1/M_0$ tumors, and Stage IV includes any $T/N_1/M_0$, any $T/N_0/M_0$, any $T/N_3/M_0$, and any T/any $N/M_1$ tumors. TNM staging for other types of tumors (for example, NSCLC tumors, such as lung SCC) is well known in the art.

Surgical resection and radiation therapy are the mainstays of treatment for most cancers (such as head and neck tumors) and remain the standard of care in most cases. For small primary cancers without regional metastases (stage I or II), wide surgical excision alone or curative radiation therapy alone is used. For more extensive primary tumors, or those with regional metastases (stage III or IV), planned combinations of pre- or postoperative radiation and complete surgical excision are generally used. Survival and recurrence risk has been roughly equivalent between surgical and radiation-based approaches. More recently, as historical survival and control rates are recognized as less than satisfactory, there has been an emphasis on the use of various induction or concomitant chemotherapy regimens.

Combinations of therapies such as one or more of lymph node dissection, pre- or post-operative radiation therapy, and chemotherapy may be administered to a subject if there is any lymph node metastasis, for example, an increase in DSG-3 protein in one or more lymph node from a subject. In general, for primary tumors presenting regional metastases (as judged by the presence of one or more lymph nodes expressing increased amount of DSG-3 protein), the standard of care involves at least the combination of pre- or postoperative radiation and complete surgical excision.

1. Lymph Node Dissection

In some examples, if an increase in DSG-3 protein is detected in a lymph node sample (such as a lymph node or portion thereof, a lymph node biopsy, or cells isolated from a lymph node), the selected therapy includes lymph node dissection (for example, removal of one or more lymph nodes or clusters of lymph nodes, such as those lymph nodes located physically nearest to the tumor site). One of skill in the art can select appropriate lymph nodes based upon the type and location of the primary tumor and/or lymph node sample.

In a particular example, if the lymph node sample exhibiting increased DSG-3 protein amount is a cervical lymph node (for example, a lymph node sample from a subject having head and neck squamous cell carcinoma), the selected therapy may include neck dissection (for example, removal of lymph nodes and surrounding tissue from the neck). The cervical lymph nodes are divided into five levels, as shown in Table 2. Neck dissection may include removal of all or some (for example 2, 3, or 4) levels of lymph nodes.

TABLE 2

Cervical lymph node levels

| Level | Lymph Nodes |
|---|---|
| 1 | Submental and submandibular nodes |
| 2 | Upper jugulodigastric group, including jugulodigastric node |
| 3 | Middle jugular nodes, including jugulo-omohyoid node |
| 4 | Inferior jugular nodes |
| 5 | Posterior triangle group, including spinal accessory nodes |

Radical neck dissection includes removal of all five levels of lymph nodes, with removal of the sternocleidomastoid muscle, jugular vein, and spinal accessory nerve. Modified radical neck dissection includes removal of all five levels of lymph nodes in the lateral neck, with preservation of one or more of the spinal accessory nerve, jugular vein, and sternocleidomastoid muscle. Selective neck dissection includes removal of lymph nodes with preservation of one or more lymph node levels. For example, selective neck dissection includes removal of levels 1-3 (supraomohyoid neck dissection) for example, for oral cavity carcinoma; removal of levels 2-4 (anterior neck dissection), for example, for hypopharyngeal or laryngeal carcinoma; or removal of levels 2-5 (anterolateral neck dissection), for example, for oropharyngeal carcinoma.

For HNSCC, neck dissection (alone or in combination with other therapies, such as pre- or post-operative radiation) may be selected for tumors with an N stage of $N_1$ or higher (such as any $T/N_1/M_0$, any $T/N_2/M_0$, any $T/N_3/M_0$, any $T/N_1/M_1$, and so on). An increase in DSG-3 protein in a lymph node relative to a control indicates that the tumor is at least stage $N_1$, even though by standard staging, the tumor may be identified as $N_0$. In some examples, radical neck dissection may be selected as a therapy for the subject if an increase in DSG-3 protein is detected in more than one lymph node (such as at least 2, 3, 4, 5, or more lymph nodes) or if an increase in DSG-3 protein of more than about 10-fold relative to the control is detected in one or more lymph node. Modified radical neck dissection may be selected as a therapy for the subject if an increase in DSG-3 protein of more than about 3-fold and less than about 10-fold relative to the control is detected in a single lymph node. Selective neck dissection may be selected as a therapy for the subject if an increase in DSG-3 protein of less than about 3-fold relative to the control is detected in a single lymph node. One of skill in the art may select the degree of neck dissection (for example, radical, modified, or selective) based on additional criteria, such as primary tumor size or location. For example, a larger primary tumor may lead to selection of a more aggressive neck dissection in a subject than a smaller primary tumor, even if the number of involved lymph nodes or amount of increase in DSG-3 protein is the same. If an increase in DSG-3 protein relative to a control is not detected in any lymph node, the selected therapy does not include neck dissection.

In another example, if the lymph node sample exhibiting increased DSG-3 protein amount is a hilar or mediastinal lymph node (for example, a lymph node sample from a subject having lung squamous carcinoma), the selected therapy may include lymph node dissection (for example, systemic or limited hilar and/or mediastinal lymph node dissection). Systemic mediastinal lymph node dissection on the right side includes all paratracheal, subcarinal, and inferior pulmonary ligament lymph nodes. Systemic mediastinal lymph node dissection on the left side includes all aortopulmonary window, subcarinal, and inferior pulmonary ligament lymph nodes.

For lung SCC, lymph node dissection (alone or in combination with other therapies, such as pre- or post-operative radiation) may be selected for tumors with an N stage of $N_1$ or higher (such as any $T/N_1/M_0$, any $T/N_2/M_0$, any $T/N_3/M_0$, any $T/N_1/M_1$, and so on). An increase in DSG-3 protein in a lymph node relative to a control indicates that the tumor is at least stage $N_1$, even though by standard staging, the tumor may be identified as $N_0$. In some examples, systemic hilar or mediastinal dissection may be selected as a therapy for the subject if an increase in DSG-3 protein is detected in more than one hilar or mediastinal lymph node (such as at least 2, 3, 4, 5, or more lymph nodes), respectively, or if an increase in DSG-3 protein of more than about 10-fold relative to the control is detected in one or more lymph node. Limited hilar and/or mediastinal dissection may be selected as a therapy for the subject if an increase in DSG-3 protein of more than about 3-fold and less than about 10-fold relative to the control in a single hilar or mediastinal lymph node, respectively. One of skill in the art may select the degree of lymph node dissection (for example, systemic or limited) based on additional criteria, such as primary tumor size or location. For example, a larger primary tumor may lead to selection of a more aggressive lymph node dissection in a subject than a smaller primary tumor, even if the number of involved lymph nodes or amount of increase in DSG-3 protein is the same. If an increase in DSG-3 protein relative to a control is not detected in any lymph node, the selected therapy does not include lymph node dissection.

2. Radiation Therapy

In another example, if an increase in DSG-3 protein (such as an increase of about 1.5-fold or more relative to a control) is detected in one or more lymph nodes, the selected therapy includes radiation therapy. In particular examples, the radiation therapy includes external beam therapy (for example, delivery of a beam of high-energy x-rays to the location of the tumor). In other examples, the radiation therapy includes intensity-modulated radiation therapy (IMRT), which is able to focus more precisely so that fewer healthy cells are destroyed than is the case with external beam therapy. IMRT reduces incidental damage to the structures near the tumor that may not be involved. Methods and therapeutic dosages of radiation therapy are known to those skilled in the art, and can be determined by a skilled clinician.

In other examples, if an increase in DSG-3 protein relative to a control is not detected in any lymph node, the selected therapy may still include radiation therapy, in order to prevent recurrence or metastasis of the primary tumor, for example metastasis to the regional lymph nodes.

3. Chemotherapeutic Agents

In another example, if an increase in DSG-3 protein (such as an increase of about 1.5-fold or more relative to a control) is detected in one or more lymph nodes, the selected therapy includes one or more chemotherapeutic agent. Chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguaninc), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin.

In a particular example, if the subject has (or had) a head and neck squamous cell carcinoma, the chemotherapeutic agent may include cisplatin, carboplatin, cetuximab, bevacizumab, erlotinib, bleomycin, paclitaxel/carboplatin or combinations thereof. In particular examples, cisplatin or cetuximab therapy (for example, cisplatin plus radiation therapy or cetuximab plus radiation therapy) may be selected for a subject if an increase in DSG-3 protein is detected in a lymph node sample from a subject with HNSCC. Alternatively, if an increase in DSG-3 protein relative to a control is not detected in any lymph node, the selected therapy may not include a chemotherapeutic agent.

In another example, if the subject has (or had) a lung squamous carcinoma, the chemotherapeutic agent may include cisplatin or carboplatin, alone or in combination with etoposide, gemcitabine, paclitaxel, vinorelbine, topotecan, or irinotecan. In a particular example, combination cisplatin/etoposide chemotherapy is selected for the subject if an increase in DSG-3 protein is detected in a lymph node sample from a subject with lung SCC. In other examples, the selected chemotherapeutic agent may include erlotinib, gefitinib, bevacizumab, alone or in combination with other chemotherapeutics, such as cisplatin or paclitaxel, if an increase in DSG-3 protein is detected in a lymph node sample from a subject with lung SCC. Alternatively, if an increase in DSG-3 protein relative to a control is not detected in any lymph node, the selected therapy may not include a chemotherapeutic agent.

In other examples, even if an increase in DSG-3 protein relative to a control is not detected in any lymph node, the selected therapy may still include one or more chemotherapeutic agent, in order to prevent recurrence or metastasis of the primary tumor, for example metastasis to the regional lymph nodes.

In some examples, the disclosed methods include providing the selected therapy (such as lymph node dissection, radiation therapy, or chemotherapeutics) to the subject. These agents (which are administered at a therapeutically effective amount) and treatments can be used alone or in combination. Methods and therapeutic dosages of such agents and treatments are known to those skilled in the art, and can be determined by a skilled clinician.

The present disclosure is illustrated by the following non-limiting Examples.

EXAMPLE 1

Detection of DSG-3 in Primary Tumors and Metastatic Lymph Nodes

This example describes detection of DSG-3 by immunohistochemistry in primary tumors and metastatic lymph nodes.

Methods

Arrays: Two tissue microarrays were assayed; LC810 (US Biomax, Rockville, Md.), a lung cancer with matched lymph node tissue array, containing 80 cores from 40 cases, and MET181 (US Biomax), a metastatic cancer tissue array containing 18 cores from 18 cases.

Antibodies: Mouse anti-human desmoglcin 3 (Cat. No. 32-6300; Invitrogen, Carlsbad, Calif.) was used at a 1:25 dilution, rabbit-anti-cytokeratin Wide Spectrum Screening (Dako, Carpinteria, Calif.) was used at 1:500; both antibodies were diluted in 2.5% PBS.

Immunohistochemistry: Paraffin sections or tissue microarrays were incubated at 65° C. for 15-30 minutes, dewaxed in 3 changes of SafeClear II™ (Fisher Scientific) for 5 minutes each, and hydrated with graded alcohols (100%, 95%, 70%), 2 changes for 5 minutes each. Endogenous peroxidase was blocked by incubating for 20 minutes in 3% $H_2O_2$ in 70% ethanol and the antigens were then retrieved in 10 mM citric acid (2.1 g/L) and heated in a microwave for 2 minutes at 100% power and 18 minutes at 20% power. The slides were allowed to cool down for 15 minutes and washed extensively with distilled water, followed by 3 changes of PBS for 5 minutes each.

After blocking with 2.5% BSA in PBS (room temperature, RT) for 30 minutes, the slides were incubated with the first antibody overnight at 4° C., washed with 3 changes of PBS for 5 minutes each, and incubated with the secondary or link antibody (biotinylated anti-rabbit immunoglobulins for cytokeratins and biotinylated anti-mouse immunoglobulins for DSG-3; Vector Laboratories, Burlingame, Calif.), 1:400, 30 minutes at RT. Following several washes with PBS, the sample was incubated with the ABC peroxidase solution (Vector Laboratories; in 2.5% BSA in PBS) for 30 minutes at RT. The slides were then extensively washed with PBS and the reaction developed with 3,3'-diaminobenzidine under microscopic control. The reaction was stopped with distilled water. Mayer's hematoxylin was used to counterstain and was washed 15 minutes in running tap water to bluish. The slides were then dehydrated in graded alcohols (70%, 95%, 100%), 2×5 minutes each, cleared in SafeClear™, and mounted in permanent mounting media.

All slides were scanned at 400× using an Aperio Scanscope® CS (Aperio, Vista, Calif.) and quantified.

Results

Figure 1B:
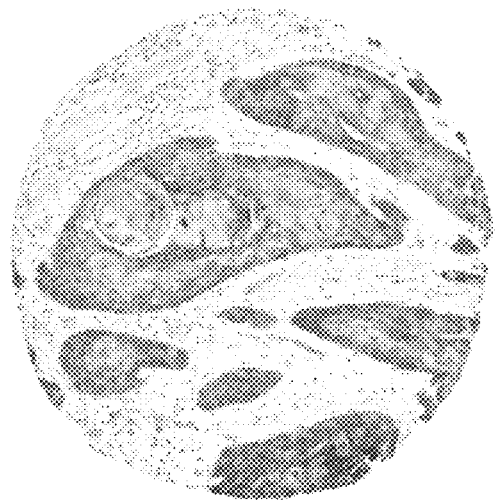
FIG. 1B is a series of digital images of DSG-3 protein detected by HIC in paired primary head and neck tumor samples and invaded lymph nodes.
Figure 1B:
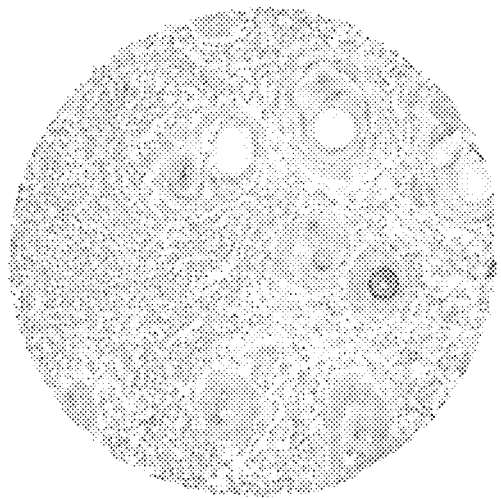
Figure 1B:
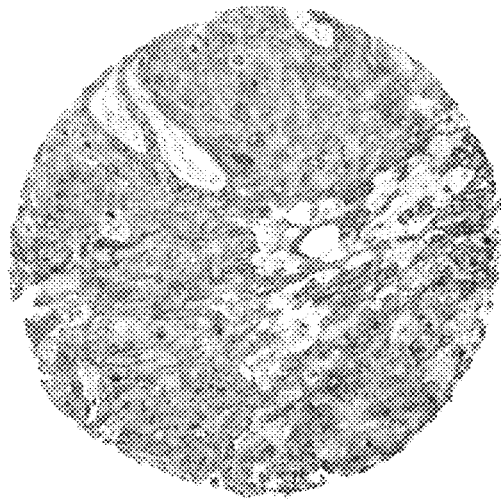
Figure 1B:
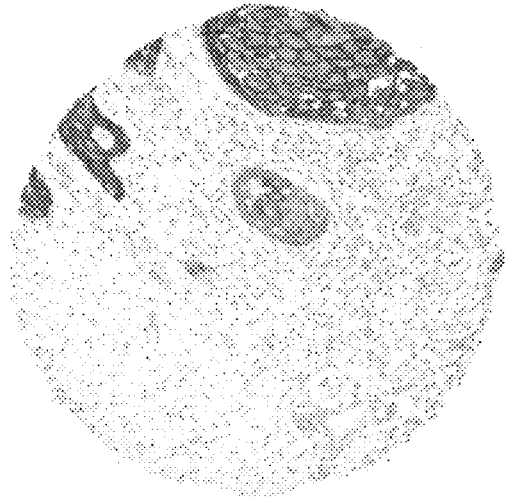

DSG-3 protein expression in primary HNSCC and negative (normal) and positive (invaded) lymph nodes (LN) was evaluated by immunohistochemistry (IHC) (FIG. 1A). DSG-3 protein was present in the primary tumor. In the invaded LN, clusters of cells containing DSG-3 protein were detected, indicating metastatic spread of the tumor. In contrast, no cells positive for DSG-3 were observed in the non-invaded normal lymph node. A total of eight samples from primary head and neck cancers and their corresponding invaded and non-invaded lymph nodes were analyzed. In every case, all invaded lymph nodes were positive for immunostaining with antibodies against DSG-3 (FIG. 1B).

Figure 2:
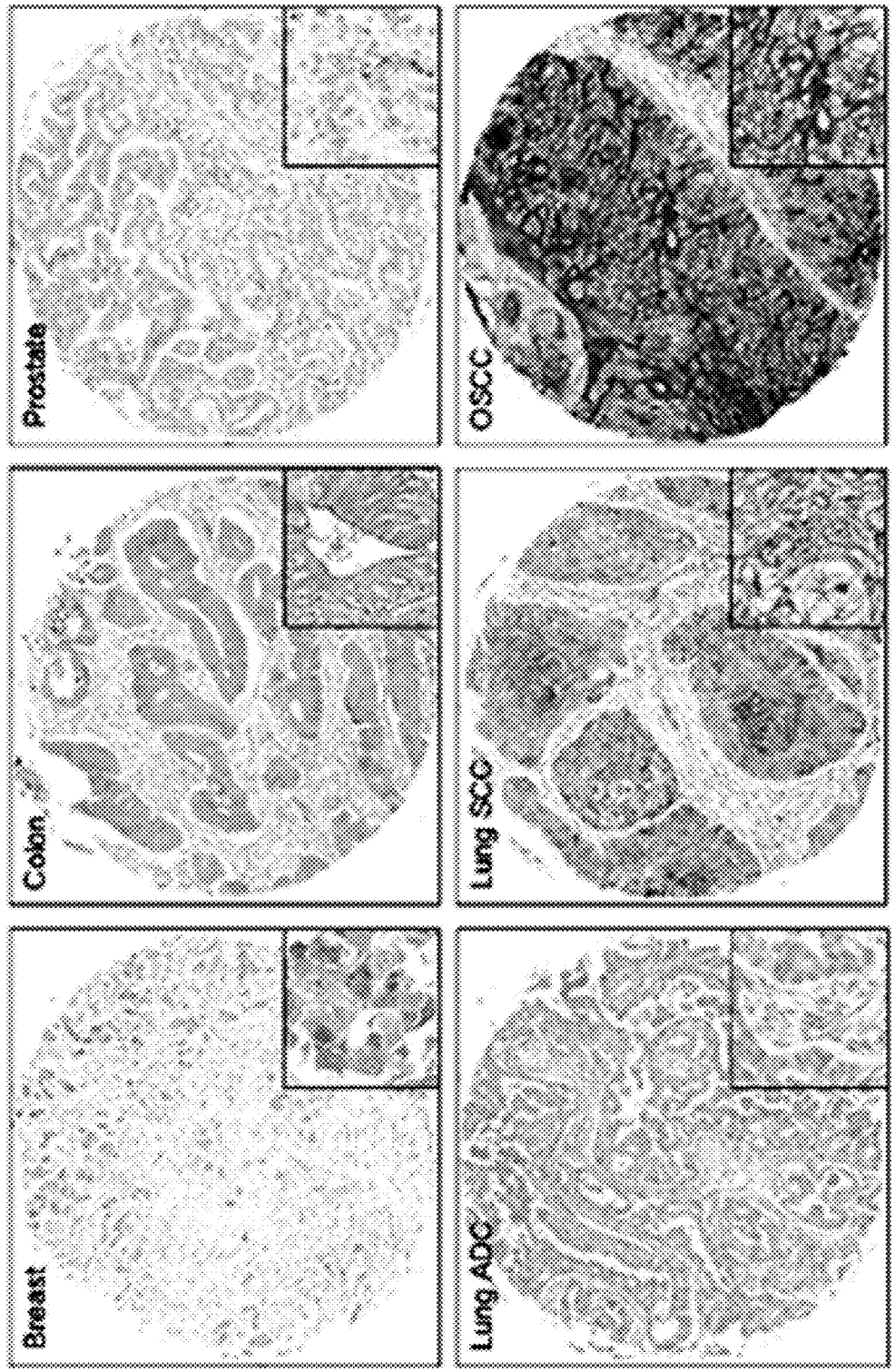
FIG. 2 is a series of digital images of DSG-3 protein detected by IHC in a tissue microarray including breast, colon, prostate, lung adenocarcinoma (ADC), lung squamous carcinoma (SCC), and oral squamous carcinoma (OSCC) samples.
Figure 3:
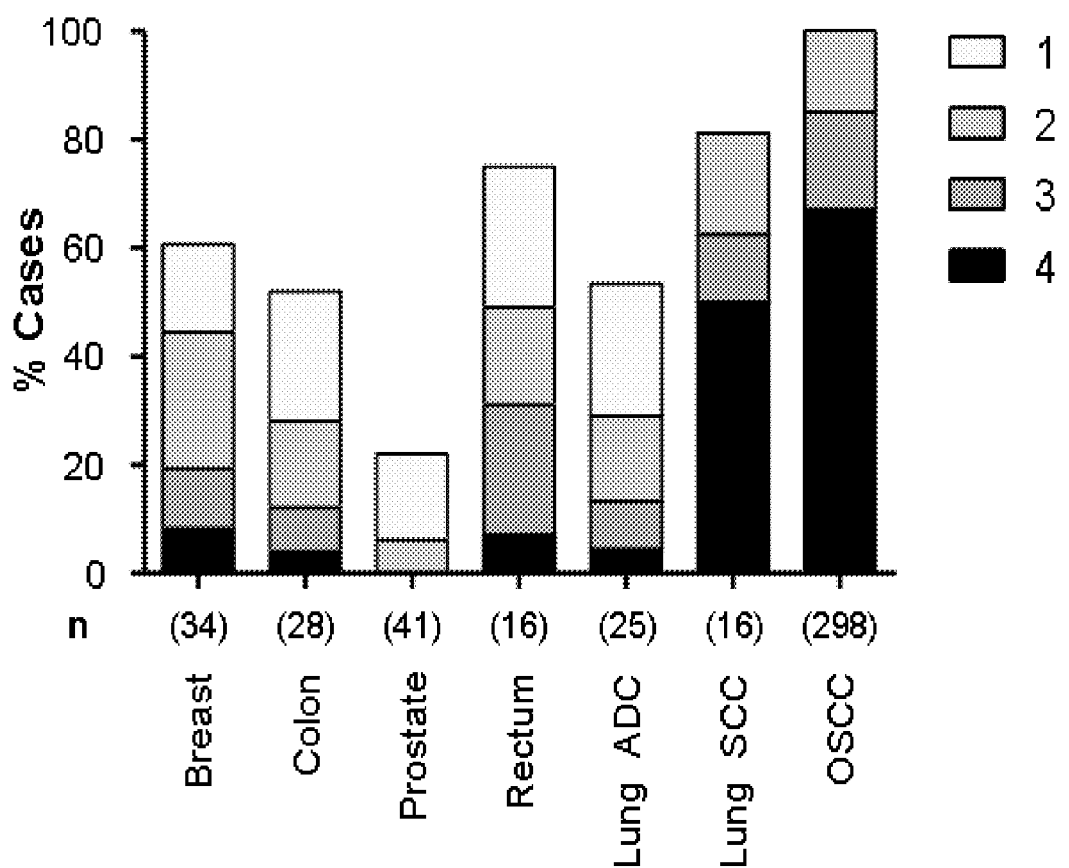
FIG. 3 is a bar graph showing intensity of DSG-3 IHC staining in the indicated cancer types. Intensity was rated from low (1) to high (4). n=number of cases analyzed for each cancer type.

DSG-3 levels were also investigated in tissue microarrays (TMAs) consisting of key cancers, including oral cavity lesions (FIG. 2). DSG-3 was highly expressed in tumors derived from cells of squamous epithelial origin, such as lung squamous carcinoma (SCC) and oral squamous carcinoma (OSCC). In contrast, DSG-3 was poorly expressed in breast and prostate cancer, as well in adenocarcinoma of the lung (ADC), which reflects their glandular origin. In colon carcinoma DSG-3 protein expression was variable. The intensity of DSG-3 staining was also evaluated in the tumors on a scale of 1 (low) to 4 (high). Tumors of squamous epithelial cell origin (lung SCC and OSCC) had much higher DSG-3 staining intensity than tumors of other cellular origin (FIG. 3).

Figure 4A:
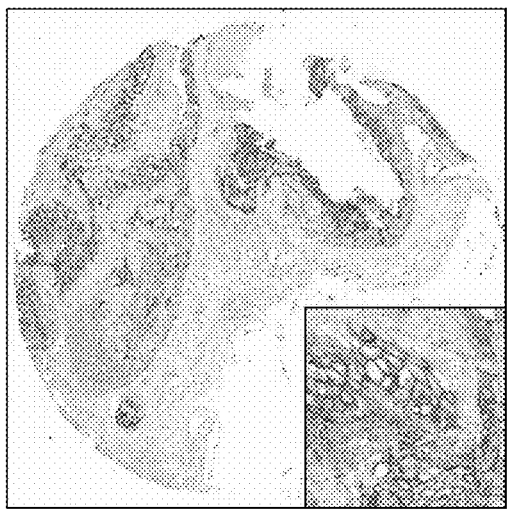
FIG. 4A, metastatic squamous cell carcinoma (inset: higher magnification showing typical membrane-associated reactivity of DSG-3)
Figure 4B:
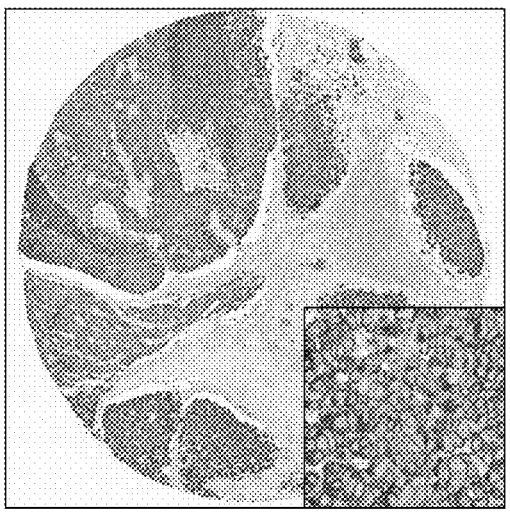
FIG. 4B, breast adenocarcinoma (inset: higher magnification showing relatively small cells of this cancer show strong membrane positivity)
Figure 4C:
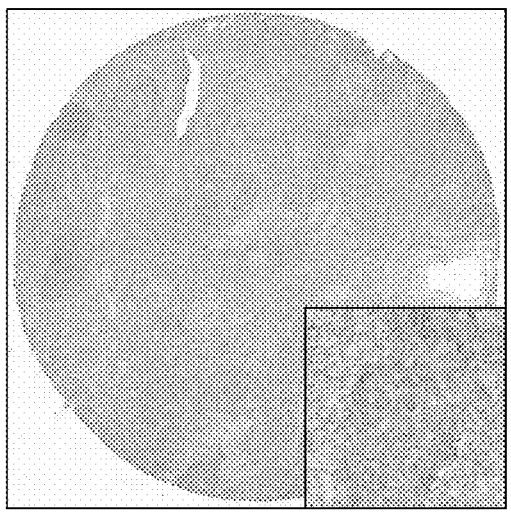
FIG. 4C, nasopharyngeal carcinoma with an isolated island of DSG-3 positive cells (inset: higher magnification showing DSG-3 reactivity was associated with the squamous epithelial component)
Figure 4D:
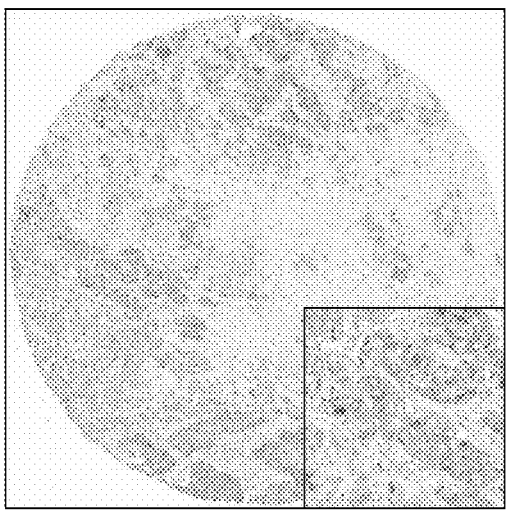
FIG. 4D, poorly differentiated colon carcinoma (inset: higher magnification showing that reactivity varies from cell to cell, but almost 90% of the tumor cells are positive).

Additional TMA cores were analyzed for DSG-3 levels by IHC. Almost all cells were positive in a metastatic squamous cell carcinoma (FIG. 4A). Strong immunoreactivity was also present in a breast adenocarcinoma (FIG. 4B). An isolated island of DSG-3 positive cells were seen at low magnification in a nasopharyngeal carcinoma; at higher magnification it was evident that this reactivity was associated with the squamous epithelial component (FIG. 4C). DSG-3 reactivity varied significantly from cell to cell in a poorly differentiated colon adenocarcinoma (FIG. 4D), but in general, almost 90% of the tumor cells were positive.

DSG-3 immunoreactivity was also measured in 78 lung tumors from the LC810 tissue microarray (2 cases in the array corresponded to reactive non-tumoral tissue). DSG-3 was positive in 23 (77%) cases of squamous cell carcinoma (SCC), in 2 (5%) adenocarcinomas, but in none of the 6 small cell lung carcinoma samples (SCLC).

Finally, DSG-3 immunoreactivity was measured in 18 samples of metastatic tissue from different tumors. The highest scores (% of cell immunoreactive for DSG-3) were seen for squamous cell carcinoma, a nasopharyngeal carcinoma in which the squamous component was highly reactive, and one breast adenocarcinoma. Positive reaction was also seen with other adenocarcinomas (Table 3).

TABLE 3

Expression of DSG-3 Protein in Metastatic Lymph Nodes

| Primary Tumor | DSG-3 (% cells stained in invaded LN) |
|---|---|
| Breast carcinoma | 0 |
| Colon adenocarcinoma | 0 |
| Colon adenocarcinoma | 0 |
| Gastric adenocarcinoma | 0 |
| Lung adenocarcinoma | 0 |
| Rectal adenocarcinoma | 0 |
| Rectal adenocarcinoma | 0 |
| Gastric adenocarcinoma | 10 |
| Breast adenocarcinoma | 20 |
| Gastric adenocarcinoma | 20 |
| Colon adenocarcinoma | 70 |
| Colon adenocarcinoma | 80 |
| Thyroid adenocarcinoma | 80 |
| Breast carcinoma | 100 |
| Lung squamous cell carcinoma | 100 |
| Lung squamous cell carcinoma | 100 |
| Nasopharyngeal carcinoma | 100 |

EXAMPLE 2

Quantitation of DSG-3 Protein in Samples

This example describes the quantitation of DSG-3 in cell lysates by Western blotting and ELISA methods.

Methods

Western blotting: Tumor cells were lysed with T-PER™ buffer (Thermo Scientific), sonicated, and followed by estimation of solubilized protein extracts. For Western blot analysis of cultured cells, 15 µg of total cellular protein content (TCL) was resolved on polyacrylamide gels, transferred onto nylon membrane and followed by blocking in 5% milk solution (dissolved in TBS-Tween® 20 solution; TBST) for 2 hours at room temperature. The membranes were incubated with primary antibody to human desmoglein-3 (hDSG-3) raised in goat (goat anti-hDSG-3; R&D Systems, Minneapolis, Minn.) at a concentration of 0.2 µg/mL in 5% bovine serum albumin (BSA) in double distilled water. Anti-mouse α Tubulin (mouse monoclonal, Santa Cruz Biotechnology, Calif.) was also used at 0.2 µg/mL in 5% BSA, to monitor equal loading of tumor cell samples. After incubation for 3 hours at room temperature, blots were quickly washed (3×1 min), followed by incubation for 45 minutes with secondary antibody labeled with HRP (donkey anti-goat and rabbit anti-mouse to detect hDSG-3 and a Tubulin, respectively), at a dilution of 1:5000 (5% milk in TSBT). After several washes (3×10 min), the membranes were subjected to chemo-luminescence to visualize the protein bands.

ELISA: Total cell lysate (TCL) was prepared from exponentially growing HaCaT cells by lysing the cells with T-PER™ buffer (Thermo Scientific), sonicating, and estimation of the solubilized protein extract. TCL was prepared in parallel from 5 µm cryosections from two samples (8T and 9T) of human oral squamous biopsies following the same procedure. Recombinant human DSG3 (rhDSG3) (R&D Systems, Minneapolis, Minn.) was used as antigen for the standard curve. Samples were diluted in 12.5 µl of 2× coating buffer (0.2 M NaHCO$_3$, pH 9.4), for a final volume of 25 µl sample in 1× coating buffer. Samples and standards were subjected in parallel to the same analysis in triplicate.

Samples were added to individual wells of ELISA plates (Costar EIA, Cat. No. 3690; Corning, Lowell, Mass.), incubated for 1 hour at 37° C., washed twice with blocking solution (SuperBlock blocking buffer in TBS, Cat#37535, Thermo Scientific/Pierce, Rockford, Ill.) and incubated with 300 µl of blocking buffer for 5 minutes at room temperature. This blocking solution was removed and wells were incubated with 25 μl of a 1:1000 dilution of 50 μg/ml biotinylated anti-hDSG3 antibody (R&D Systems, Cat. No. BAF1720) in blocking buffer for 1 hour at 37° C., washed 10 times with 200 μl of PBS/0.05% Tween® 20, and incubated with 25 μl of secondary antibody preparation (1:12,000 streptavidin-HRP (Cat. No. 21130, Thermo Scientific/Pierce, Rockford, Ill.) in blocking buffer) for 1 hour at 37° C. Wells were washed 10 times with 200 μl of PBS/0.05% Tween® 20, and treated with 50 μl of the substrate solution (Cat. No. WBKLS0500, Millipore, Billerica, Mass.). Luminescence was measured in a 96-well plate luminometer (1 second reading time).

Results

Figure 5:
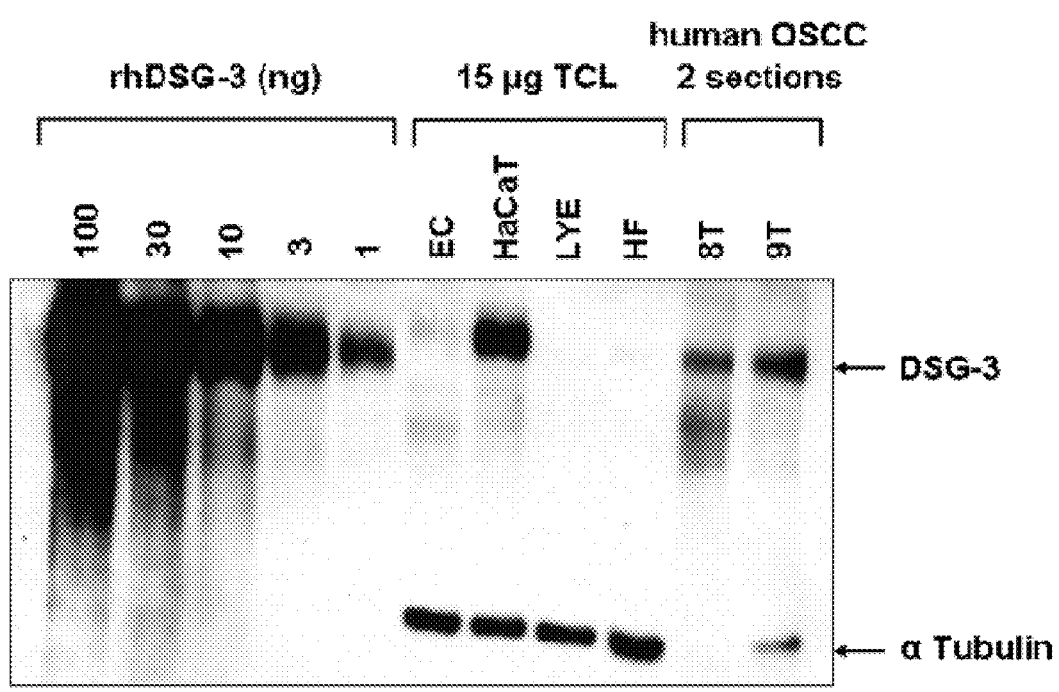
FIG. 5 is a digital image of a Western blot detecting DSG-3 protein. rhDSG-3 is recombinant human DSG-3 protein; the number of ng loaded is indicated above the lanes. 15 µg of total cell lysate (TCL) from endothelial cells (EC), an immortalized tumor cell line (HaCaT), lymphatic cells (LYE), and human fibroblast cells (HF) was loaded on the gel. TCL from 5 µm sections of two human OSCC tumor biopsies (8T, 9T) was also loaded.

The presence of DSG-3 protein in tumor cells was confirmed by Western blotting. DSG-3 protein was present in a squamous cell line (HaCaT, an immortalized epidermal squamous tumoral cell line), but not in non-squamous cells (human lymphatic cells, LYE (Lonza, Allendale, N.J.); human endothelial cells, EC; and human fibroblast cells, HF) (FIG. 5). In addition, two cryosections of human oral squamous (8T and 9T) biopsies expressed DSG-3 protein. The level of endogenously expressed DSG-3 protein in the cells and tumor samples was compared with amounts of recombinant human DSG-3 standards loaded on the same blot (rhDSG-3; R&D Systems, Minneapolis, Minn.). Approximately 1 ng of hDSG-3 could be detected in TCL extracted from the tumor cryosections and approximately 3 ng of DSG-3 could be detected in the HaCaT cell line (FIG. 5).

Figure 6A:
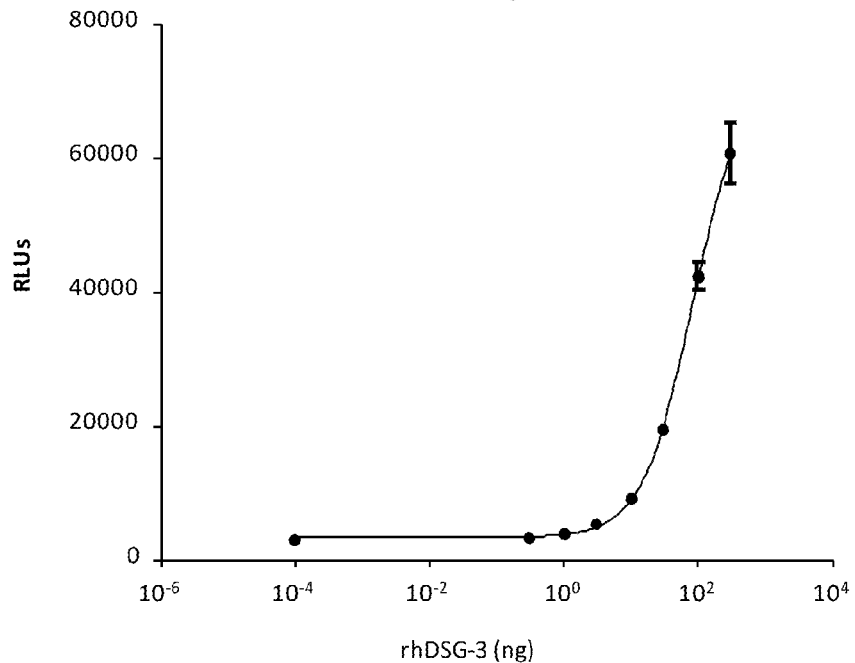
FIG. 6A is a graph showing relative luminescence units (RLU) of the indicated amounts of recombinant human DSG-3 (rhDSG-3) detected by ELISA.
Figure 6B:
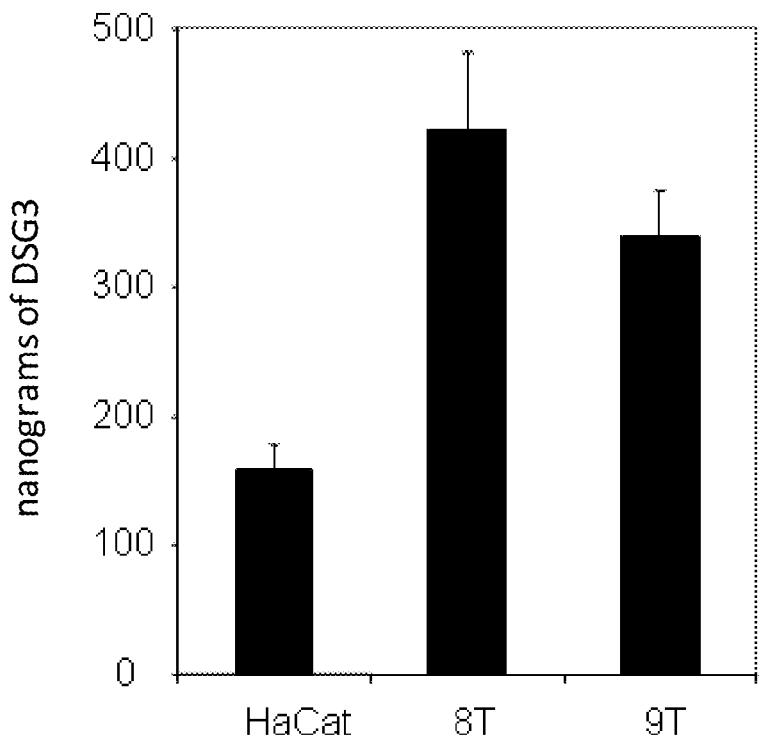
FIG. 6B is a bar graph showing the amount of DSG-3 present in HaCaT cell and OSCC samples (8T and 9T), detected by ELISA.

An ELISA assay was developed to quantify DSG-3 protein levels in cell lysates. A standard curve was established using recombinant human DSG-3. Amounts of DSG-3 from about 0.3-300 ng were detectable using this ELISA (FIG. 6A). DSG-3 content in HaCaT tumor cells and sections from OSCC tumors 8T and 9T was measured using the ELISA assay. The lower limit of detection using this method was about 10 ng, which was the amount detected in about 200 tumor cells. The HaCaT sample contained about 150 ng of DSG-3 per 10 μg cell lysate, while the OSCC samples contained about 300-400 ng DSG-3 per 10 μg cell lysate (FIG. 6B).

EXAMPLE 3

Sensitive Detection of DSG-3 Protein by ELISA

This example demonstrates that a small number of DSG-3 protein-expressing cells can be detected in a sample containing a large number of cells that do not express DSG-3.

Methods

Serial dilutions of TCL from human head and neck tumor biopsies were made in TCL from a lymphocyte cell line (Jurkat cells) for ELISA detection of DSG-3 protein. TCL from an invaded lymph node from HNSCC patient (5 μg TCL from 3 biopsy cryosections), non-invaded lymph node (5 μg TCL from 3 biopsy cryosections), and Jurkat cells (control) were also tested for DSG-3 protein by ELISA. ELISA was performed as described in Example 2.

For comparison with quantitative PCR methods, HaCaT cells were diluted with Jurkat cells so that the total number of cells was kept at 10,000. Cells were pelleted from the cell mixture and RNA was extracted with TRIZOL® reagent (Invitrogen) following the manufacturer's recommended procedure. RNA was quantitated, and 200 ng was used to prepare cDNA using SuperScript® III (Invitrogen) following manufacturer's recommendations. The resulting products were then used as a template to set up quantitative PCR (qPCR) reactions, which consisted of one μg of cDNA, together with specific primers to DSG-3 and iQ™ SYBR Green Supermix (Bio-Rad, Hercules, Calif.). The reactions were read using the iCycler® (Bio-Rad).

Results

Figure 7:
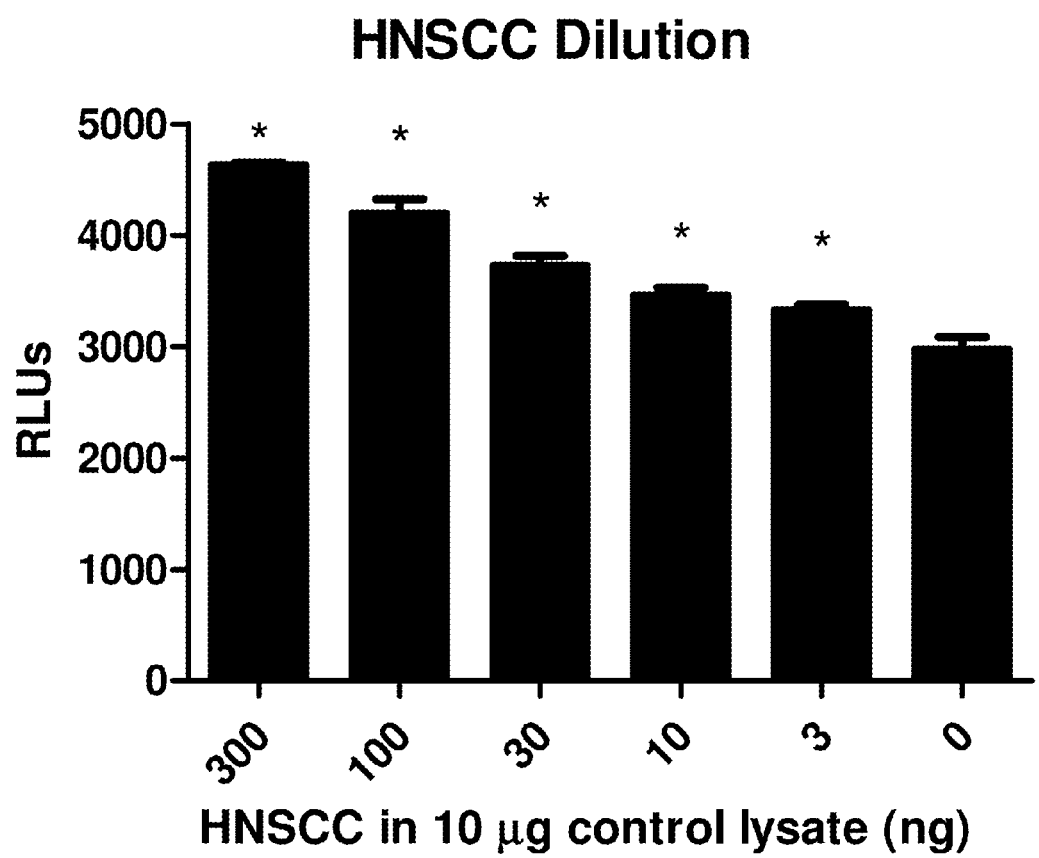
FIG. 7 is a bar graph showing RLU of DSG-3 detected by ELISA in the indicated amount of HNSCC TCL diluted in 10 µg of TCL from control lymphocyte (Jurkat) cells. * indicates p<0.01 with respect to 0 ng HNSCC TCL.

Serial dilutions of lysates from human head and neck cancer tumor biopsies into lysates from a lymphocyte cell line (Jurkat cells; control lysate) were made. It was assumed that 1 mg protein (TCL) is equivalent to $10^6$ cells, hence 10 μg of protein represents 10,000 cells, 1 μg protein represents 1,000 cells, and 1 ng protein corresponds to 1 cell. The ELISA method was able to detect DSG-3 protein in as little as 3 ng of tumor cell lysate in 10 μg of control cell lysate, equivalent to 3 cells in 10,000 cells (FIG. 7).

Figure 8:
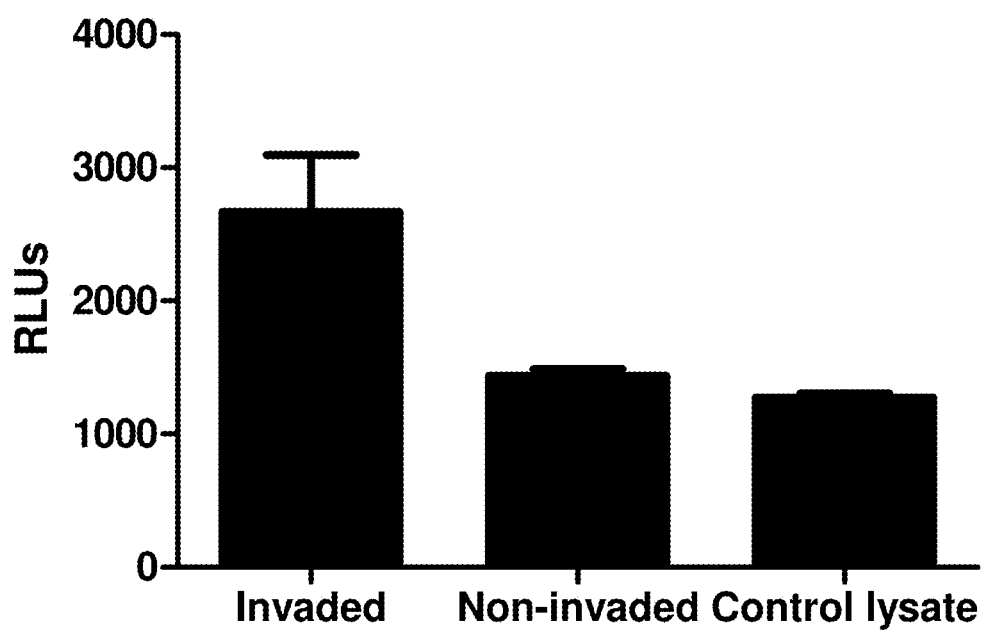
FIG. 8 is a bar graph showing RLU of DSG-3 detected by ELISA in 5 µg of TCL from invaded lymph node biopsy cryosections, non-invaded lymph node biopsy cryosections, and control (Jurkat) cells.

Using this ELISA method, DSG-3 protein expression in invaded lymph node biopsy (from HNSCC patient), non-invaded lymph node biopsy, and control (Jurkat) cell lysates was determined Non-invaded lymph node did not have increased DSG-3 compared to control (Jurkat) cell lysate (FIG. 8). However, invaded lymph node had substantially increased DSG-3 compared to the control cells and non-invaded lymph node (FIG. 8). This data reflects the highly sensitive nature of the DSG-3 ELISA and demonstrates that DSG-3 protein is increased in lymph node containing HNSCC metastasis.

Figure 9:
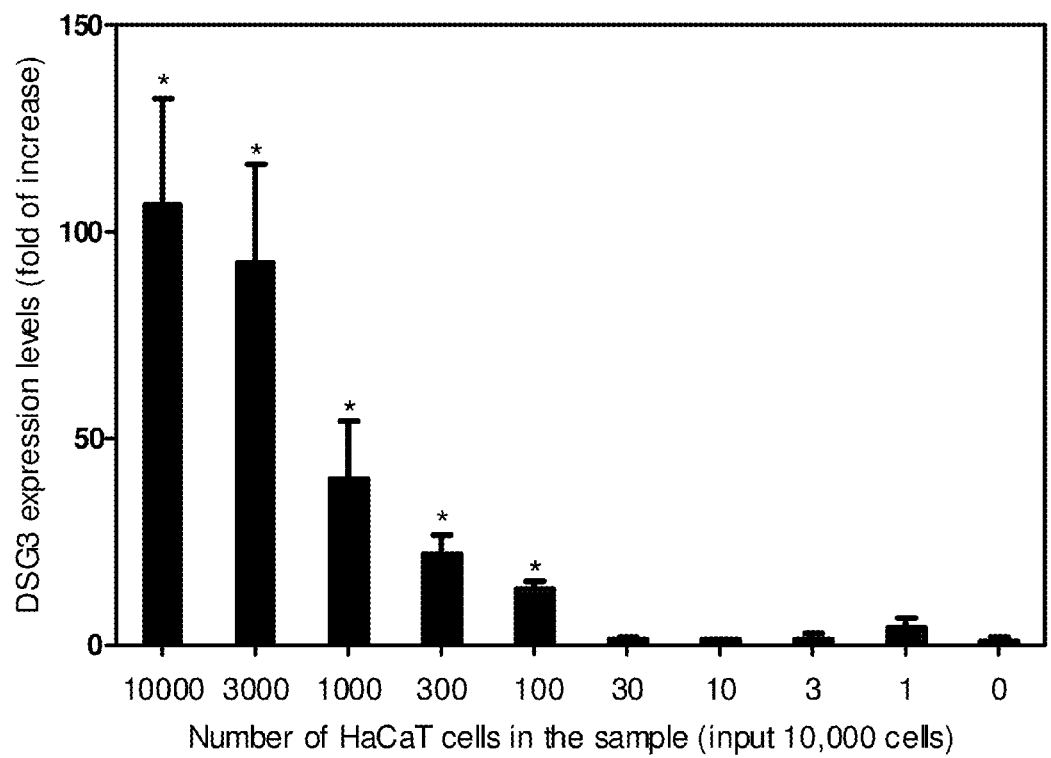
FIG. 9 is a bar graph showing detection of DSG-3 RNA expression by quantitative PCR in a mixture of HaCaT cells and Jurkat cells (10,000 cells total per sample). Detection of DSG-3 RNA in less than 100 cells in the mixture was not statistically significant. * p≤0.001.

To compare the sensitivity of the ELISA method to detection of DSG-3 RNA with qPCR, squamous cells (HaCaT cells) were diluted with control lymphocytes (Jurkat cells), keeping the total number of cells constant at 10,000. RNA was isolated from the cell mixture, and qPCR with DSG-3 specific primers was performed. Using this indirect approach (involving the processing of the RNA, its conversion to cDNA, and indirect determination after cDNA amplification), the limit of detection was about 100 squamous cells (FIG. 9), in contrast to the detection of as few as 3 cells using the ELISA method.

EXAMPLE 4

Detection of DSG-3 Protein by Electrochemical Immunoassay

This example describes exemplary methods that can be used to detect DSG-3 protein in a sample utilizing electrochemical immunoassay. However, one skilled in the art will appreciate that methods that deviate from these specific methods can also be used to successfully detect DSG-3 protein in a sample by electrochemical immunoassay.

Gold nanoparticle (AuNP) electrodes are prepared by layer-by-layer assembly of layers of poly(diallydimethylammonium chloride) (PDDA) and AuNPs on pyrolytic graphite (PG). Glutathione protected AuNPs (GSH-AuNP) are prepared by reduction of gold salt using sodium borohydride in the presence of glutathione (Zheng and Huang, J. Am. Chem. Soc. 126:12047-12054, 2004). Electrodes are prepared by placing PDDA solution (2 mg/ml in 0.05 M NaCl) on a PG disk surface to adsorb positively charged PDDA as a precursor layer. After washing with water, GSH-AuNPs (2 mg/ml) is placed on this electrode to adsorb the negatively charged GSH-AuNP layer. The final bilayer results after water washing and drying in a nitrogen stream.

Anti-DSG-3 antibodies are attached to the AuNP electrode by incubating the electrodes prepared above with 400 mM 1-(3-(dimethylamino)-propyl)-3-ethylcarbodiimide hydrochloride (EDC) and 100 mM N-hydroxysulfosuccinimide (NHSS) for 10 minutes, followed by washing. Primary anti-human DSG-3 antibody (e.g., Cat. No. 32-6300; Invitrogen/Life Technologies, Carlsbad, Calif.) in pH 7.0 PBS buffer containing 0.05% Tween® 20 is incubated with the electrode for 3 hours. Unbound antibody is removed by washing with PBS/Tween® 20 and PBS for 3 minutes each.

Secondary antibody-bead-HRP conjugates ($Ab_2$-HRP beads) are prepared by mixing carboxyl-functionalized magnetic beads (2 mg) (Polysciences, Warrington, Pa.) dispersed in 1 ml of 50 mM MES buffer, pH 5.2 with 3.2 mg of EDC at room temperature for 5 minutes. The resulting mixture is magnetically separated and washed with 50 mM MES buffer. Detection anti-DSG-3 antibody (e.g., Cat. No. MAB1720; R&D Systems, Minneapolis, Minn.; 0.01 mg/ml) and HRP (1.2 mg/ml) are added to the bead mixture and mixed for 16 hours at RT. The reaction mixture is magnetically separated and the particles resuspended in 1 M glycine, pH 8.0 and mixed for 30 minutes. The beads are washed in PBS buffer pH 7.0 several times and dispersed in pH 7.0 PBS buffer with 0.05% Tween® 20. The conjugate is diluted five-fold in PBS/Tween® 20 prior to use.

The AuNP immunosensors prepared as described above are blocked with 0.4% (w/v) casein in PBS/Tween®-20 for 1 hour. After thorough rinsing, sample (such as cell lysates from a tumor or lymph node sample) is incubated on the sensor surface for 1.25 hours at RT. After several washes with PBS, the electrode is exposed to $Ab_2$-HRP beads in buffer containing 0.05% Tween® 20 for a further 1.25 hours. The sensors are rinsed thoroughly with PBS/Tween® 20 and PBS, then placed in an electrochemical cell containing PBS buffer with 1 mM hydroquinone, holding applied potential at −0.3 V and rotating at 3000 rpm. $H_2O_2$ is injected to 0.04 mM, while measuring the amperometric current. The amount of DSG-3 protein in the sample is determined by comparing the detected current to a standard curve.

Preliminary experiments indicate that 0.1-5 pg/ml DSG-3 can be detected using this method.

EXAMPLE 5

Detecting Lymph Node Metastasis of a Tumor

This example describes exemplary methods that can be used to detect metastasis of a tumor to lymph nodes in a subject with a tumor, such as a squamous cell carcinoma. However, one skilled in the art will appreciate that methods that deviate from these specific methods can also be used to successfully detect lymph node metastasis of a tumor.

According to the teachings herein, metastasis of a tumor can be determined by directly detecting increased DSG-3 protein in a lymph node sample obtained from a subject with a tumor (e.g., a squamous cell carcinoma, such as HNSCC or lung SCC). The presence of increased amount of DSG-3 protein in one or more lymph node indicates that the tumor has metastasized to the lymph node.

In one particular example, lymph node tissue samples (such as from regional lymph nodes) can be collected, for example, by fine needle aspirate or open biopsy. In one example, a total cell lysate is prepared by lysing the cells with T-PER™ buffer (Thermo Scientific/Pierce, Rockford, Ill.) and sonicating the lysate. DSG-3 protein is detected by a conventional ELISA assay utilizing an anti-DSG-3 primary antibody (such as BAF1720, R&D Systems, Minneapolis, Minn.; for example as described in Example 2) or by an electrochemical immunoassay utilizing AuNPs (for example, as described in Example 4). The amount of DSG-3 protein in the sample is compared to a control (such as a control sample or a reference value). Detecting an at least 1.5-fold increase (such as at least 1.5-fold, 2-fold, 3-fold, 4-fold, 5-fold, 10-fold, or more increase) in DSG-3 protein amount as compared to a non-metastatic control sample or reference value (e.g., expected levels or range of levels of DSG-3 protein in a non-metastatic lymph node) indicates that the subject has a metastasis of the tumor.

EXAMPLE 6

Diagnostic Test for Lymph Node Metastasis

This example describes an exemplary diagnostic test, for example in a clinical setting, for detecting metastasis of a tumor to a lymph node of a subject. However, one skilled in the art will appreciate that methods that deviate from these specific methods can also be used to successfully detect lymph node metastasis of a tumor.

In some embodiments, the test includes directly determining an amount of desmoglein-3 protein in a lymph node sample in a subject, for example as described in Example 5. The results of the test are provided to a user (such as a clinician or other health care worker, laboratory personnel, or patient) in a perceivable output that provides information about the results of the test. In some examples, the output can be a paper output (for example, a written or printed output), a display on a screen, a graphical output (for example, a graph, chart, voltammetric trace, or other diagram), or an audible output. In one example, the output is one or more voltammetric traces obtained utilizing an electrochemical immunoassay, such as a AuNP immunosensor. The size of the voltammetric trace is proportional to the amount of DSG-3 protein in the sample.

In other examples, the output is a numerical value, such as an amount of DSG-3 protein in the sample or a relative amount of DSG-3 protein in the sample as compared to a control. In additional examples, the output is a graphical representation, for example, a graph that indicates the value (such as amount or relative amount) of DSG-3 protein in the sample from the subject on a standard curve. In a particular example, the output (such as a graphical output) shows or provides a cut-off value or level that indicates the presence of metastasis if the value or level of DSG-3 protein in the sample is above the cutoff and absence of metastasis if the value or level of DSG-3 protein in the sample is below the cut-off. In some examples, the output is communicated to the user, for example by providing an output via physical, audible, or electronic means (for example by mail, telephone, facsimile transmission, email, or communication to an electronic medical record).

The output can provide quantitative information (for example, an amount of DSG-3 protein or an amount of DSG-3 protein relative to a control sample or value) or can provide qualitative information (for example, a diagnosis of presence or absence of a metastasis, a likelihood of metastasis, or a prognosis). In additional examples, the output can provide qualitative information regarding the relative amount of DSG-3 protein in the sample, such as identifying presence of an increase in DSG-3 protein relative to a control, a decrease in DSG-3 protein relative to a control, or no change in DSG-3 protein relative to a control.

In some examples, the output is accompanied by guidelines for interpreting the data, for example, numerical or other limits that indicate the presence or absence of metastasis. The guidelines need not specify whether metastasis is present or absent, although it may include such a diagnosis. The indicia in the output can, for example, include normal or abnormal ranges or a cutoff, which the recipient of the output may then use to interpret the results, for example, to arrive at a diagnosis, prognosis, or treatment plan. In other examples, the output can provide a recommended therapeutic regimen (for example, based on the amount of DSG-3 or the amount of increase of DSG-3 relative to a control, as described in Example 7 below), such as lymph node dissection (for example, radical, modified, or selective lymph node dissection), radiation therapy, chemotherapy, or a combination thereof.

In some examples, the test may include determination of other clinical information (such as determining the amount of one or more additional cancer biomarkers in the sample). In some examples, the test includes an array, such as an antibody array or an electrochemical immunosensor array and the output of the test includes quantitative or qualitative information about DSG-3 protein (such as the amount of DSG-3 protein or an amount of change of DSG-3 protein relative to a control, or a relative increase or decrease of DSG-3 protein compared to the control), as well as quantitative or qualitative information about one or more additional proteins.

EXAMPLE 7

Selection of Therapy

This example describes exemplary methods for selecting therapy for a subject with metastasis of a tumor, based on detection of lymph node DSG-3 protein.

Metastasis of a tumor (such as a HNSCC or lung SCC tumor) to the lymph nodes can be detected as described in Example 5. Surgical resection of the primary tumor is performed, if possible.

If an increase in DSG-3 protein is detected in more than one lymph node (such as at least 2, 3, 4, 5, or more lymph nodes) or if an increase in DSG-3 protein of more than about 10-fold relative to the control is detected in one or more lymph node, extensive lymph node dissection (such as radical neck dissection for HNSCC or systemic mediastinal dissection for lung SCC) is selected as a therapy for the subject. If an increase in DSG-3 protein of more than about 3-fold and less than about 10-fold relative to the control is detected in a single lymph node, less extensive lymph node dissection (such as modified radical neck dissection for HNSCC or limited mediastinal dissection for lung SCC) is selected. If an increase in DSG-3 protein of about 3-fold or less relative to the control is detected in a single lymph node, selective lymph node dissection (such as selective neck dissection) is selected.

Radiation therapy may also be selected, for example, if there is any metastasis to the regional lymph nodes, as detected by an increase in DSG-3 protein amount. In addition, chemotherapy (such as cisplatin or cetuximab) may be selected if there is any detectable lymph node metastasis. Combinations of therapies such as one or more of lymph node dissection, pre- or post-operative radiation therapy, and chemotherapy may also be administered to a subject if there is any lymph node metastasis, as detected by an increase in DSG-3 protein in one or more lymph node from a subject. In general, for primary tumors presenting regional metastases, for example, by the presence of lymph nodes expressing increased amount of DSG-3 protein, the standard of care involves the combination of pre- or postoperative radiation and complete surgical excision.

In view of the many possible embodiments to which the principles of the disclosure may be applied, it should be recognized that the illustrated embodiments are only examples, and should not be taken as limiting the scope of the invention. Rather, the scope of the invention is defined by the following claims. We therefore claim as our invention all that comes within the scope and spirit of these claims.

We claim:

1. A method for detecting metastasis of a squamous cell carcinoma in a subject, comprising:
   directly determining an amount of desmoglein-3 protein by electrochemical immunoassay in a lymph node sample from the subject, wherein the electrochemical immunoassay utilizes at least one anti-desmoglein-3 antibody that specifically binds an epitope in the desmoglein-3 extracellular domain;
   comparing the amount of desmoglein-3 protein in the sample to a control, wherein an increase in the amount of desmoglein-3 protein detected by electrochemical immunoassay in the sample from the subject relative to the control indicates metastasis of the squamous cell carcinoma to the lymph node, and wherein an increase in the amount of desmoglein-3 protein in a lymph node sample containing 1-100 cells with increased amount of desmoglein-3 protein is detectable by the electrochemical immunoassay; and
   treating the subject with lymph node dissection if a metastasis of the squamous cell carcinoma to the lymph node is detected by the increase in the amount of desmoglein-3 protein determined by the electrochemical immunoassay.

2. The method of claim 1, wherein the squamous cell carcinoma comprises head and neck squamous cell carcinoma or lung squamous cell carcinoma.

3. The method of claim 1, wherein the squamous cell carcinoma expresses desmoglein-3 protein.

4. The method of claim 1, wherein the lymph node is one to which metastatic spread of the squamous cell carcinoma would be expected.

5. The method of claim 4, wherein the lymph node is a regional lymph node or a sentinel lymph node.

6. The method of claim 1, wherein the anti-desmoglein-3 antibody is BAF1720 or MAB1720.

7. The method of claim 1, wherein the electrochemical immunoassay comprises:
   contacting the lymph node sample from the subject with an gold nanoparticle electrode conjugated with the anti-desmoglein-3 antibody that specifically binds an epitope in the desmoglein-3 extracellular domain;
   contacting the mixture of the lymph node sample and the gold nanoparticle electrode conjugated with the anti-desmoglein-3 antibody with magnetic beads conjugated with a secondary antibody and horseradish peroxidase; and
   detecting the amount of desmoglein-3 protein by applying an amperometric current in the presence of a horseradish peroxidase substrate.

8. The method of claim 1, wherein if the amount of desmoglein-3 protein in the sample is increased more than 10-fold relative to the control, the lymph node dissection is radical neck dissection if the squamous cell carcinoma is head and neck squamous cell carcinoma, or the lymph node dissection is systemic mediastinal lymph node dissection if the squamous cell carcinoma is lung squamous cell carcinoma.

9. The method of claim 1, wherein if the amount of desmoglein-3 protein in the sample is increased about 3-fold to about 10-fold relative to the control, the lymph node dissection is modified radical neck dissection if the squamous cell carcinoma is head and neck squamous cell carcinoma, or the lymph node dissection is limited hilar and/or mediastinal lymph node dissection if the squamous cell carcinoma is lung squamous cell carcinoma.

10. The method of claim 1, wherein if the amount of desmoglein-3 protein in the sample is increased about 3-fold or less relative to the control, the lymph node dissection is selective radical neck dissection if the squamous cell carcinoma is head and neck squamous cell carcinoma.

11. The method of claim 1, further comprising providing a test output to a user.

* * * * *